United States Patent [19]
Ordman

[11] Patent Number: 5,932,226
[45] Date of Patent: *Aug. 3, 1999

[54] METHOD AND KIT FOR DETERMINING THE OPTIMUM DOSAGE LEVEL OF PHYSIOLOGICALLY USEFUL SUBSTANCES

[75] Inventor: Alfred B. Ordman, Beloit, Wis.

[73] Assignee: Harry M. Weiss, Phoenix, Ariz.; a part interest

[*] Notice: This patent is subject to a terminal disclaimer.

[21] Appl. No.: 08/709,258

[22] Filed: Sep. 10, 1996

Related U.S. Application Data

[63] Continuation-in-part of application No. 08/317,311, Oct. 3, 1994, Pat. No. 5,558,870.

[51] Int. Cl.⁶ .......................... A61K 9/20; A61K 31/375; A61K 45/00
[52] U.S. Cl. ............................. 424/400; 424/464
[58] Field of Search .................... 424/400, 464; 514/161, 400, 464, 474

[56] References Cited

U.S. PATENT DOCUMENTS

| | | | |
|---|---|---|---|
| 3,178,451 | 4/1965 | Reyes | 549/325 |
| 3,215,602 | 11/1965 | Diamond | 514/474 |
| 3,396,226 | 8/1968 | Cavalli et al. | 514/474 |
| 5,070,085 | 12/1991 | Markham | 514/161 |
| 5,558,870 | 9/1996 | Ordman | 424/400 |
| 5,639,471 | 6/1997 | Chait et al. | 424/439 |

FOREIGN PATENT DOCUMENTS 2169202  7/1986  United Kingdom.

OTHER PUBLICATIONS

Physicians Desk Reference, 36th Edition, 1982, pp. 953, 1339.

*Primary Examiner*—Robert H. Harrison
*Attorney, Agent, or Firm*—Harry M. Weiss; Janine R. Novatt; Harry M. Weiss & Associates, P.C.

[57] ABSTRACT

A test kit and method for determining the optimal level of intake for an individual of a useful substance—including vitamin C and calcium—that is water soluble, urine excretable, and nontoxic at physiologically beneficial levels is disclosed.

5 Claims, 18 Drawing Sheets

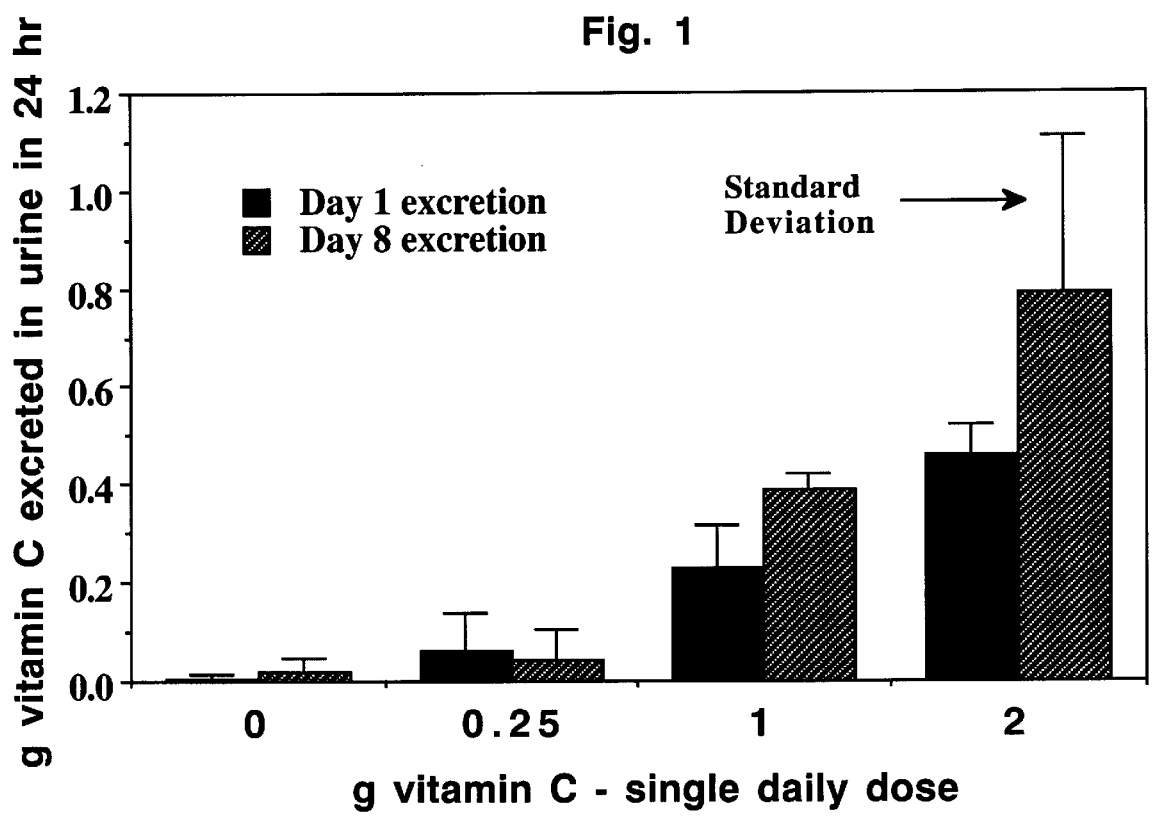

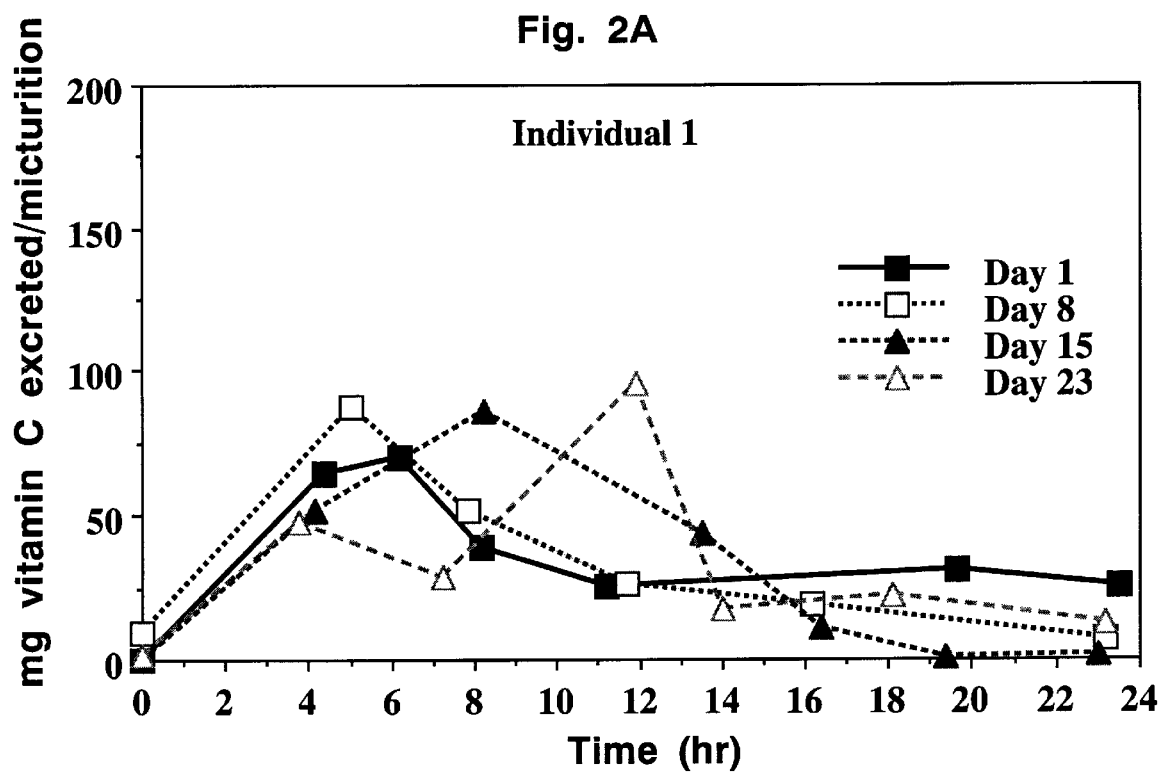

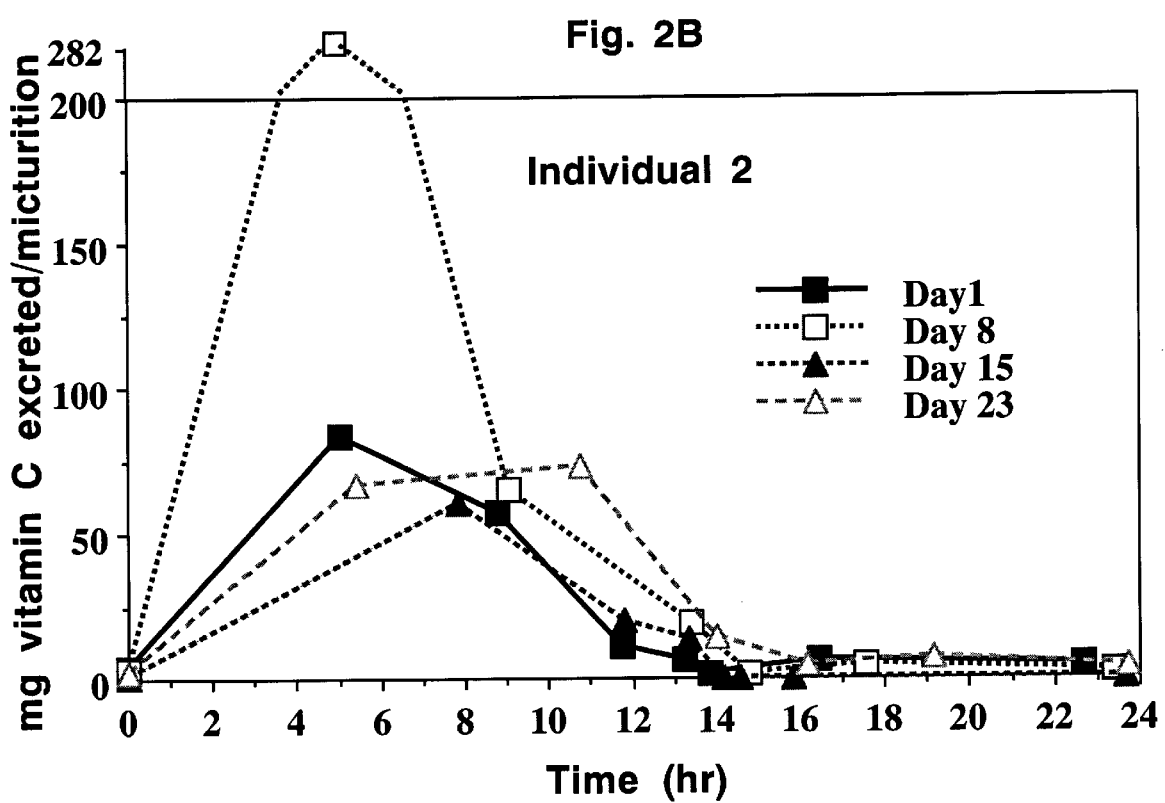

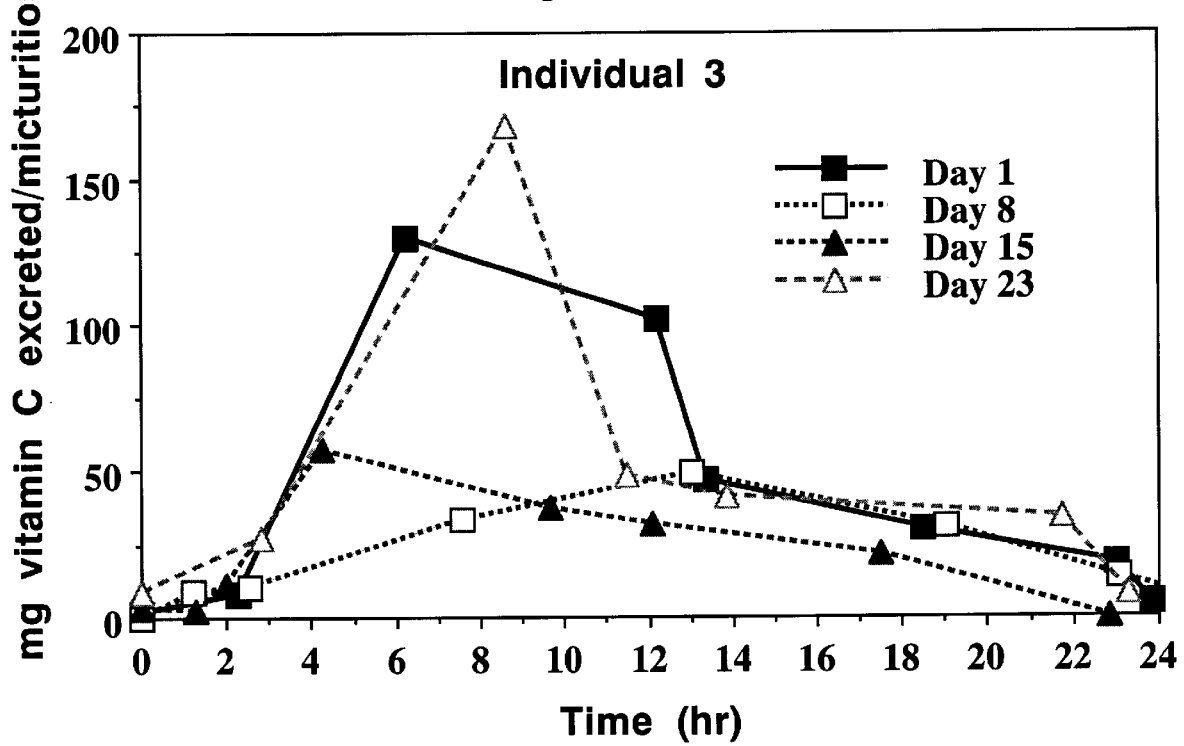

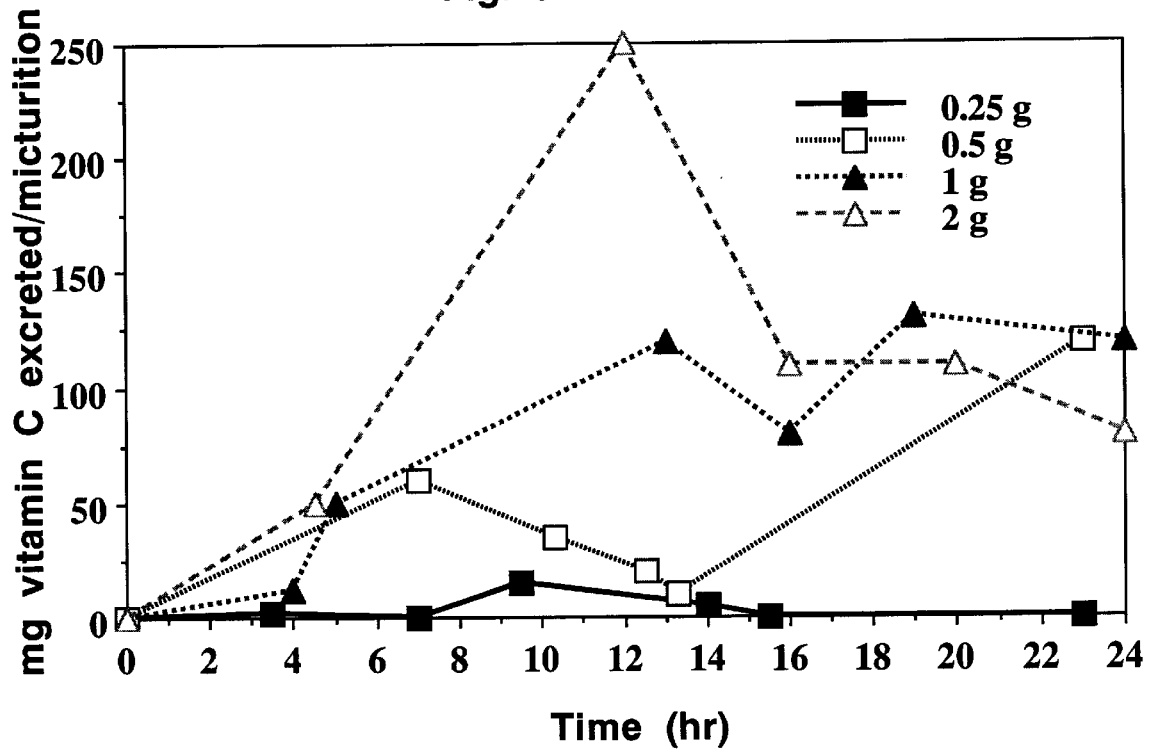

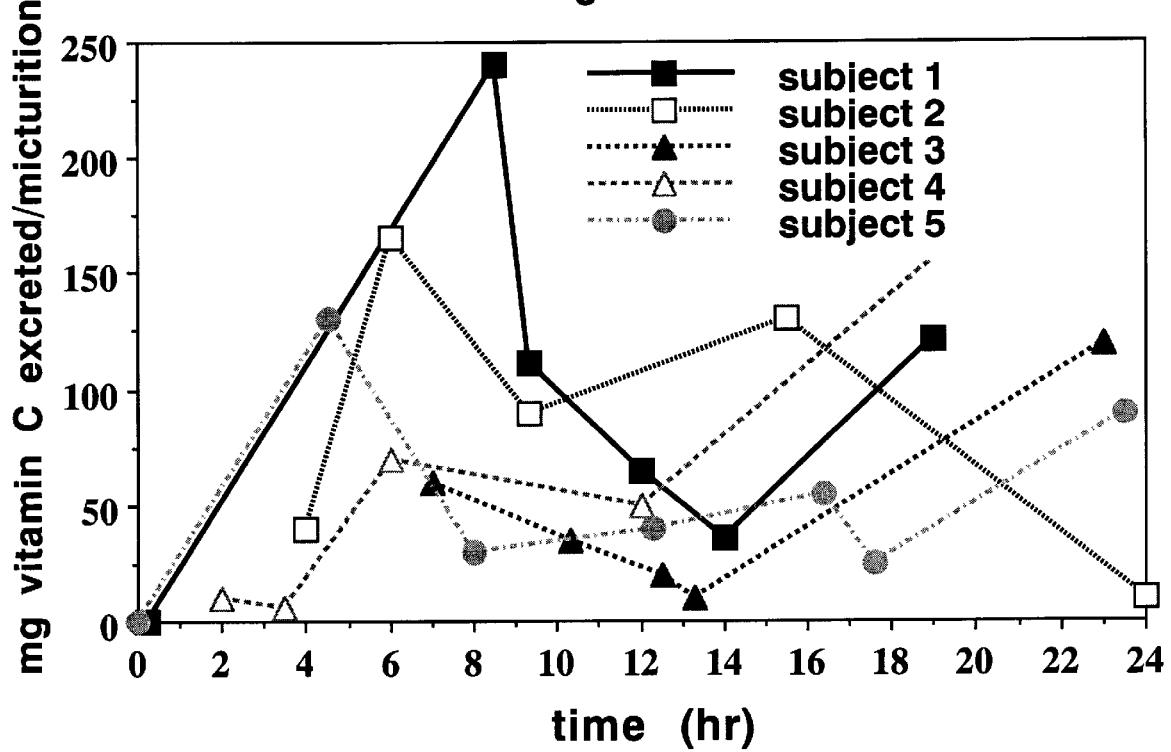

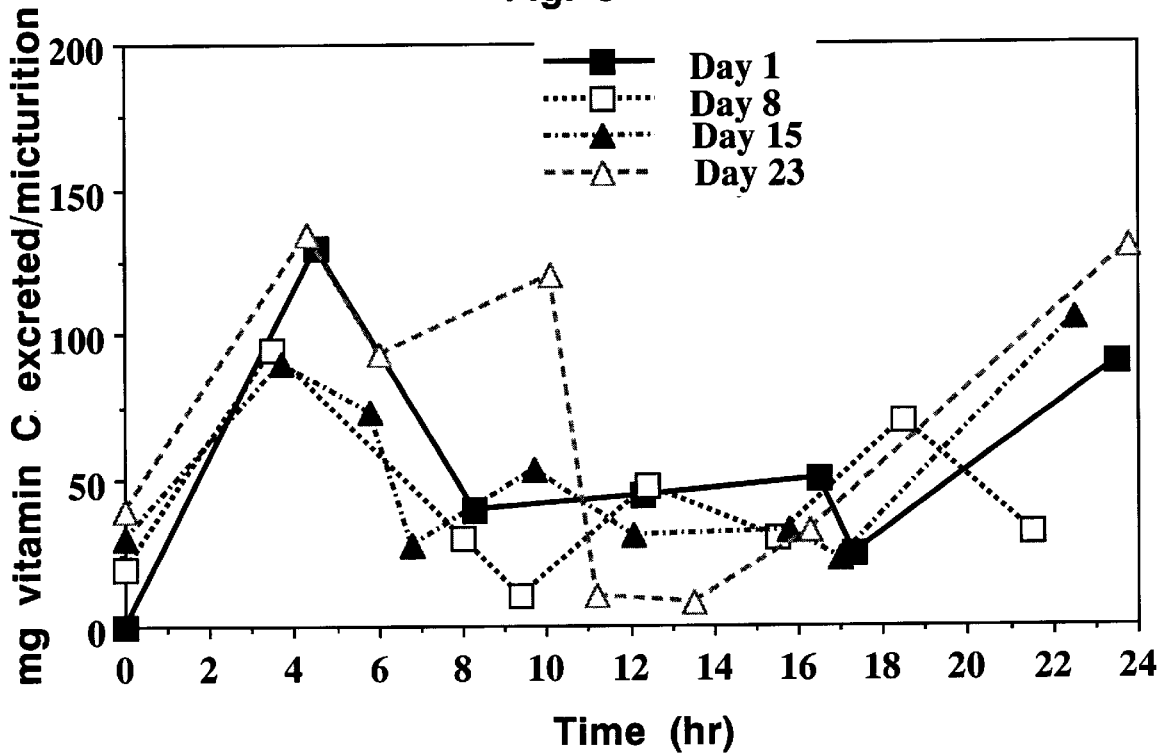

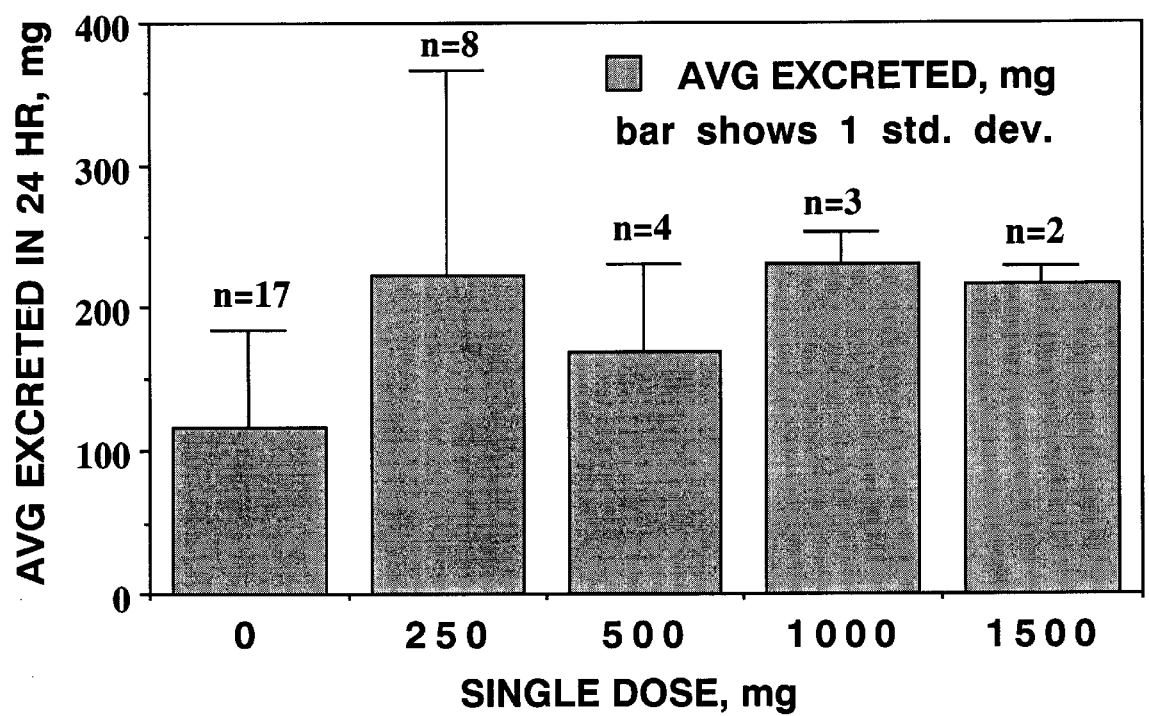

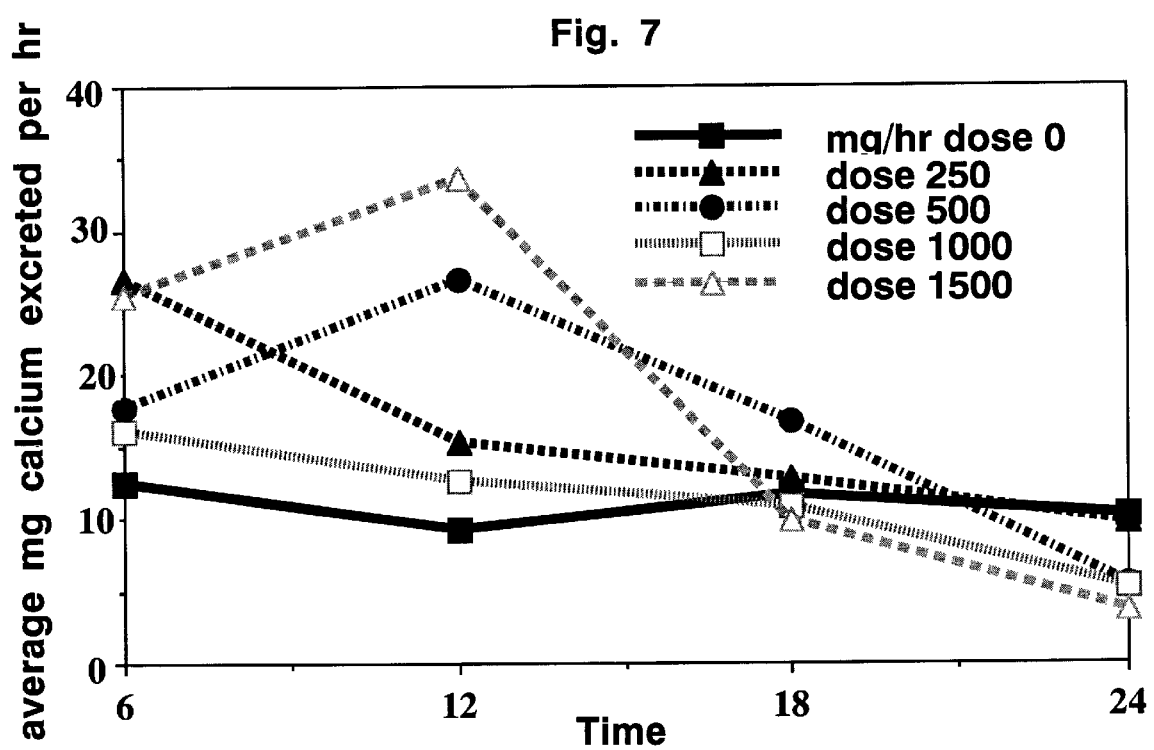

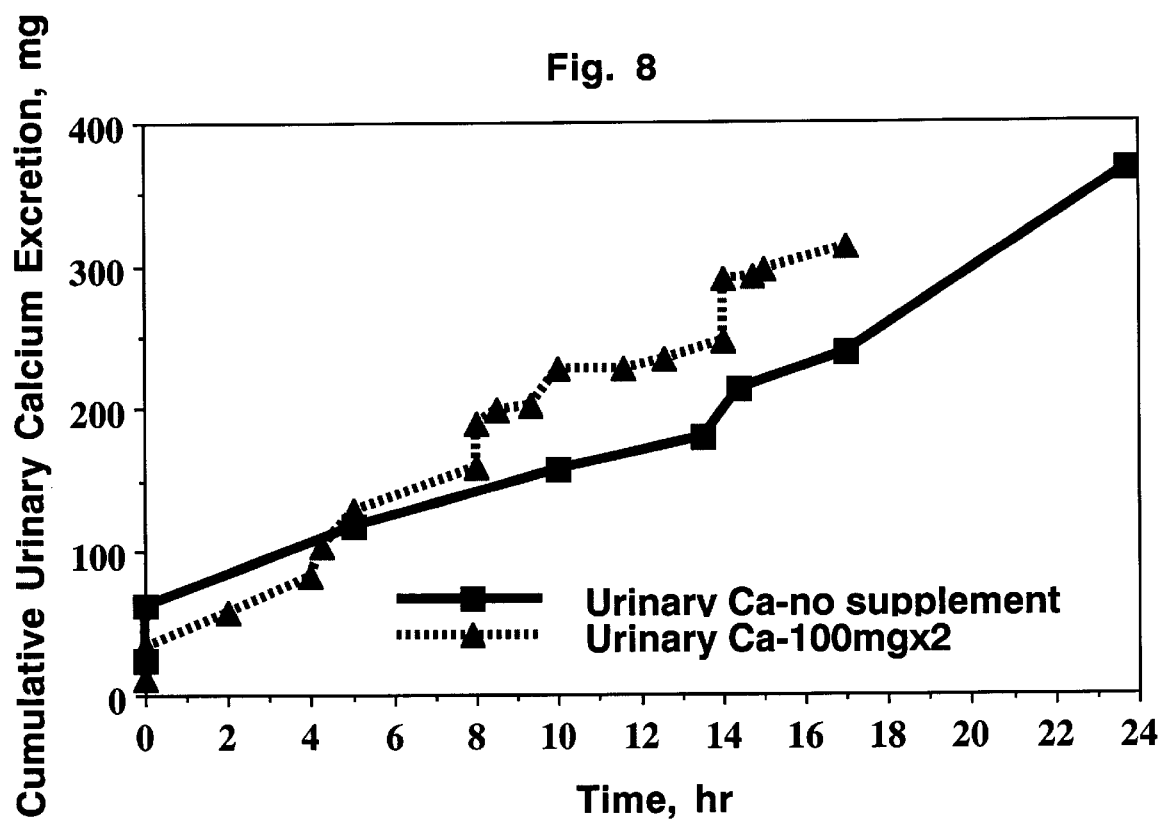

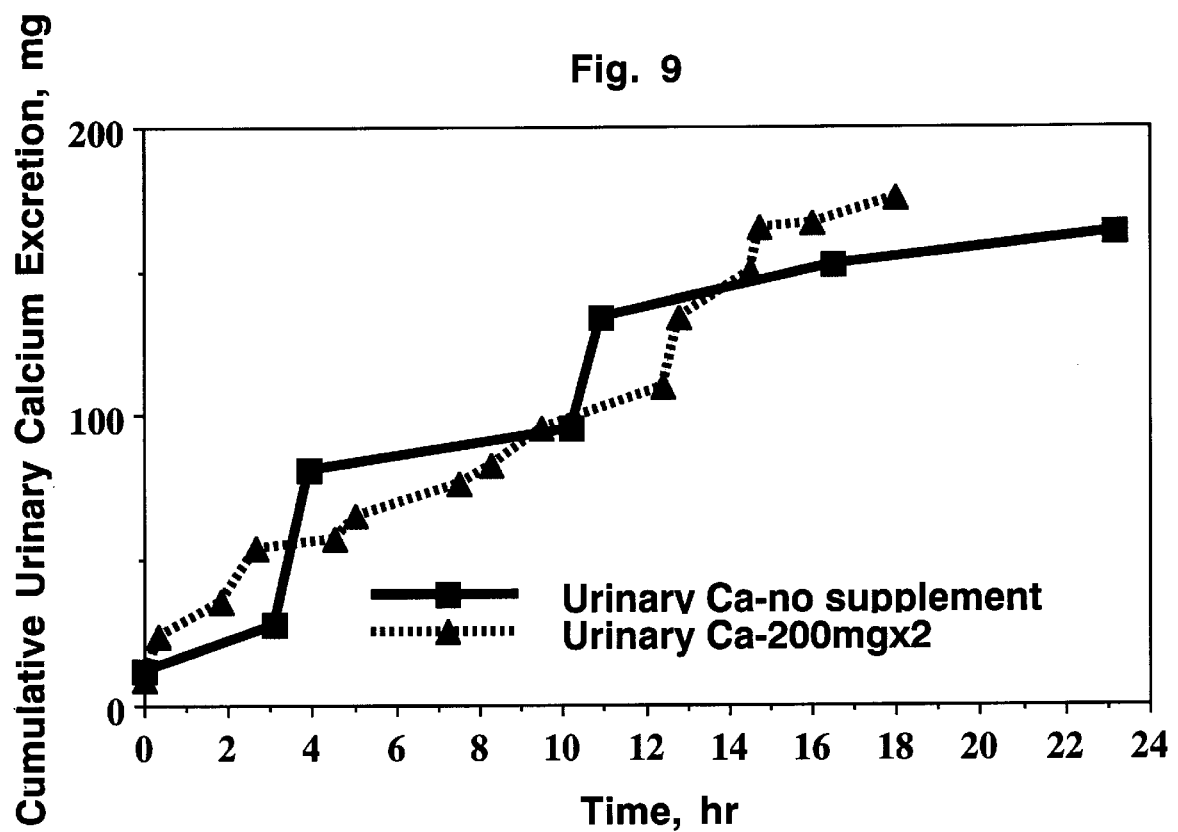

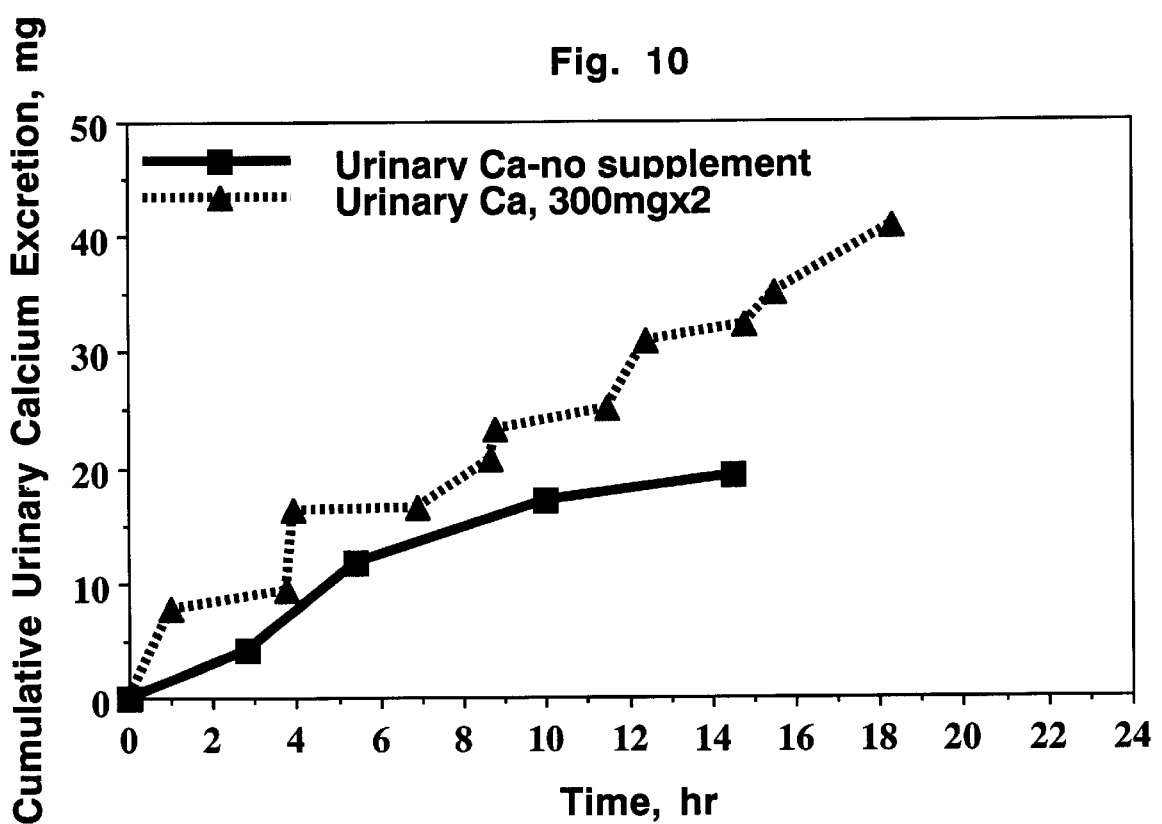

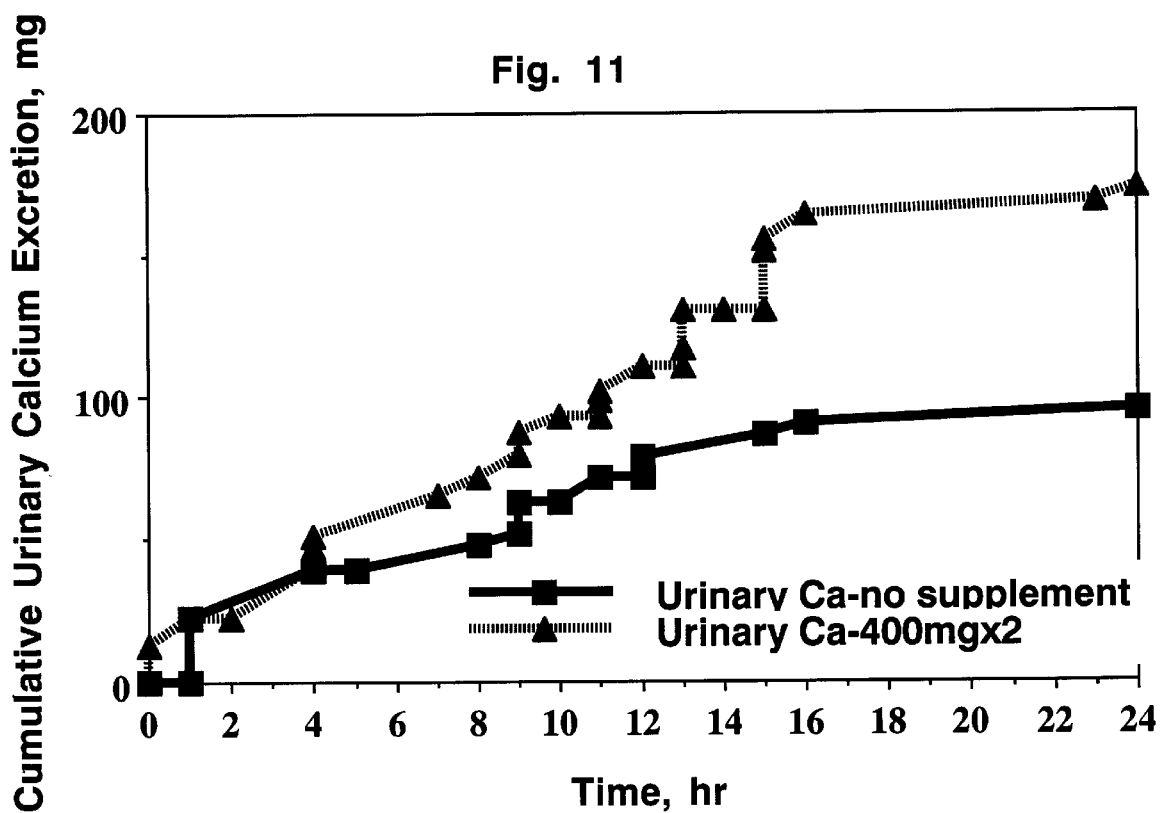

METHOD AND KIT FOR DETERMINING THE OPTIMUM DOSAGE LEVEL OF PHYSIOLOGICALLY USEFUL SUBSTANCES

CROSS-REFERENCE TO RELATED APPLICATION

This is a continuation-in-part of U.S. patent application Ser. No. 08/317,311, filed Oct. 3, 1994, now U.S. Pat. No. 5,558,870, in the name of the Applicant, to which priority is claimed.

FIELD OF THE INVENTION

This invention is related in general to the oral administration of water-soluble medication and nutritional supplements, referred to herein as edible compositions. Detailed descriptions of the application of the invention to methods for assuring optimal intake of vitamin C and calcium are provided as examples of the invention.

DESCRIPTION OF THE RELATED ART

Calcium in the diet is important in preventing osteoporosis. Osteoporosis is a bone disease that affects millions of Americans. It is estimated to cause 1.3 million fractures annually to people over age 45 in the U.S. (Bergman D. Nutrition and Bone Disorders. in *Total Nutrition,* ed. Herbert V, Subak-Sharpe G J. New York: St. Martin's Press; 1995:593–5; Nelson M. The Effects of Exercise on Bone Health and Body Composition. *AGE* 1993; 1 6:182.) Most Americans do not get sufficient calcium in their diets, creating an increased risk of osteoporosis. Guidance on whether to take calcium supplements is therefore needed.

Although one is likely to think of calcium intake as the most important variable in determining a person's risk of developing osteoporosis, a review of the literature shows that the impact of calcium intake is highly controversial, while many other factors are clear. Behavior of young adults has a major impact on the chance of developing osteoporosis later in life. Risk of osteoporosis depends on peak bone mass, which develops when young. Exercise reduces the risk for osteoporosis by increasing bone mass. (Nelson M. The Effects of Exercise on Bone Health and Body Composition. *AGE* 1993; 1 6:182.3; NIH Panel urges increase in adult calcium intake. *Pub Health Repts.* 1994; 109:715–6.) Conversely, smoking increases one's risk by reducing bone density. (NIH Panel urges increase in adult calcium intake. *Pub Health Repts.* 1994; 109:715–6; Mazess R B, Barden H S. Bone density in premenopausal women: effects of age, dietary intake, physical activity, smoking, and birth-control pills. *Am J Clin Nutr.* 1991; 53:132–42.)

Dietary factors are also significant. High protein intake causes excretion of calcium, and the high level of protein in most American's diets is probably a major cause of osteoporosis. (Holl M G, Allen L H. Comparative effects of meals high in protein, sucrose, or starch on human mineral metabolism and insulin secretion. *Am J Clin. Nutr.* 1988; 48:1219–25; Linkswiler H M, Joyce C L, Anand C R. Calcium retention of young adult males as affected by level of protein and of calcium intake. *Trans NY Acad Sci.* 1974; 36: 333–40; Anand C R, Linkswiler H M. Effect of protein intake on calcium balance of young men given 500 mg calcium daily. *J Nutr.* 1974; 1 04:695–700; Kim Y, Linkswiler H M. Effect of level of Protein Intake on Calcium Metabolism and on Parathyroid and Renal Function in the Adult Human Male. *J Nutr.* 1979; 1 09:1399–1405.) High sodium intake also leads to loss of calcium. (Itoh R, Suyama Y. Sodium excretion in relation to calcium and hydroxproline excretion in a healthy Japanese population. *Am J Clin Nutr.* 1996; 63:735–40: Castenmiller J, Mensink R P, van der Heijden L, Kouwenhoven T, Hautvast J, de Leeuw P W, Schaafsma G. The effect of Dietary sodium on urinary calcium and potassium excretion in normotensive men with different calcium intakes. *Am J Clin Nutr.* 1985; 41:52–60.)

The level of calcium intake necessary to develop optimal bone mass remains controversial. Some calcium is important in the diet to reduce the risk of osteoporosis. (Bergman D. Nutrition and Bone Disorders. in *Total Nutrition,* ed. Herbert V, Subak-Sharpe G J. New York: St. Martin's Press; 1995:593–5; Nelson M. The Effects of Exercise on Bone Health and Body Composition. *AGE* 1993; 1 6:182.; NIH Panel urges increase in adult calcium intake. *Pub Health Repts.* 1994; 109:715–6; Mazess R B, Barden H S. Bone density in premenopausal women: effects of age, dietary intake, physical activity, smoking, and birth-control pills. *Am J Clin Nutr.* 1991; 53:132–42; Holl M G, Allen L H. Comparative effects of meals high in protein, sucrose, or starch on human mineral metabolism and insulin secretion. *Am J Clin. Nutr.* 1988; 48:1219–25; Linkswiler H M, Joyce C L, Anand C R. Calcium retention of young adult males as affected by level of protein and of calcium intake. *Trans NY Acad Sci.* 1974; 36:33–340; Anand C R, Linkswiler H M. Effect of protein intake on calcium balance of young men given 500 mg calcium daily. *J Nutr.* 1974; 1 04:695–700; Kim Y, Linkswiler H M. Effect of level of Protein Intake on Calcium Metabolism and on Parathyroid and Renal Function in the Adult Human Male. *J Nutr.* 1979; 1 09:1399–1405; Itoh R, Suyama Y. Sodium excretion in relation to calcium and hydroxproline excretion in a healthy Japanese population. *Am J Clin Nutr.* 1996; 63:735–40; Castenmiller J, Mensink R P, van der Heijden L, Kouwenhoven T, Hautvast J, de Leeuw P W, Schaafsma G. The effect of Dietary sodium on urinary calcium and potassium excretion in normotensive men with different calcium intakes. *Am J Clin Nutr.* 1985; 41:52–60; Heaney R P, Gallagher J C, Johnston C C, Neer R, Parfitt A M, Whedon G D. Calcium Nutrition and bone health in the elderly. Am J Clin Nutr. 1982; 36:986–1013; Consensus Conference. NIH Panel urges increase in adult calcium intake. *Pub Health Repts.* 1994; 109:715–6. Reid I R, Ames R W, Evans M C, Gamble G D, Sharpe S J. Effect of calcium supplementation on bone loss in postmenopausal women. *New Eng J Med.* 1993; 328:460–4.) Osteoporosis. JAMA 1984; 252: 799–802.) The nutritional requirement for calcium of 1,000–1,500 mg per day is widely reported to be beneficial. (NIH Panel urges increase in adult calcium intake. *Pub Health Repts.* 1994; 109:715–6; Reid I R, Ames R W, Evans M C, Gamble G D, Sharpe S J. Effect of calcium supplementation on bone loss in postmenopausal women. *New Eng J Med.* 1993; 328:460–4.) In the U.S., half the men over age 35 and about 85% of women over age 20 do not achieve these levels. (Reid I R, Ames R W, Evans M C, Gamble G D, Sharpe S J. Effect of calcium supplementation on bone loss in postmenopausal women. *New Eng J Med.* 1993; 328:460–4.) However, many societies with much lower calcium intake have lower rates of osteoporosis. (Mazess R B, Barden H S. Bone density in premenopausal women: effects of age, dietary intake, physical activity, smoking, and birth-control pills. *Am J Clin Nutr.* 1991; 53:132–42; Hegsted D M. Calcium and Osteoporosis. *J Nutr.* 1986; 1 16:2316–2319.) The source of calcium may also be a critical variable. Milk, a well-known source of calcium, may actually suppress absorption and increase excretion of calcium. (Hegsted D M. Calcium and Osteoporosis. *J Nutr.* 1986; 1 16:2316–2319;

Lewis N M, Marcus M S K, Behling A R, Greger J L. Calcium supplements and milk. *Am J Clin Nutr.* 1989; 49:527–33.) On the other hand, whole wheat has been shown to be a very good source of calcium. (Randall T. Longitudinal study pursues questions of calcium, hormones, and metabolism in life of skeleton. *JAMA* 1992; 268:2357–8; Weaver C M, Heaney R P, Martin B R, Fitzsimmons M L. Human Calcium Absorption From Whole-Wheat products. *JNutr.* 1991; 1769–75.)

Although calcium is important in the diet, it also is dangerous for many individuals. (Itoh R, Suyama Y. Sodium excretion in relation to calcium and hydroxproline excretion in a healthy Japanese population. *Am J Clin Nutr.* 1996; 63:735–40.). Contraindications for calcium include allergies to calcium or antacids, kidney stones, high blood-calcium level, sarcoidosis, kidney disease, chronic diarrhea, or irregular heartbeat. In addition, calcium interacts with more than 20 different medications. Calcium also has undesirable side-effects, including appetite loss, constipation, headache, high blood pressure, and nausea.

One way to increase calcium intake is the use of dietary supplements, but whether this reduces the risk of osteoporosis is unclear. Some studies have shown that supplements are absorbed as effectively as calcium from milk (Sheikh M S, Santa Ana C A, Nicar M J, Schiller L R, Fordtran J S. Gastrointestinal absorption of calcium from milk and calcium salts. *N Eng. J Med.* 1987; 317:532–6; Mortensen L, Charles P. Bioavailability of calcium supplements and the effect of vitamin D. *Am J Clin Nutr.* 1996; 63:354 7; Recker R R, Bammi A, Barger-Lux M J, Heaney R P. Calcium absorbability from milk products, an imitation milk, and calcium carbonate. *Am J Clin Nutr.* 1988; 47:93–5.) and that the type of calcium in the supplement does not affect absorption (Randall T. Longitudinal study pursues questions of calcium, hormones, and metabolism in life of skeleton. *JAMA* 1992; 268:2357–8; Johnson R N. A study of five calcium supplements. *Eur J Clin Nutr.* 1991; 45:117–9.), but other results conflict with these (Need A G, Horowitz M, Morris H A, Nordin B E C. Effects of three different calcium preparations on urinary calcium and hydroxyproline excretion in postmenopausal-osteoporotic-women. *EurJClinNutr,* 1991; 4:357–361; Nicar M J, Pak C Y C. Calcium bioavailability from calcium carbonate and calcium citrate. *J Clin Endocrin Met.* 1985; 61:391–393.) It is also unclear whether high calcium intake results in increased bone mass. (Riis B, Thomsen K, Christiansen C. Does calcium supplementation prevent postmenopausal bone loss?. *N Eng J Med.* 1987; 316:173–7.) There is evidence that calcium is absorbed more effectively in young people than in mature adults (Dawson-Hughes B. Calcium and vitamin D nutrition and Aging. *AGE* 1993; 16:180; Herbert V. Vitamins and Minerals plus Antioxidant Supplements. in *Total Nutrition,* ed. Herbert V, Subak-Sharpe G J. New York: St. Martin's Press; 1995:112.), and thus intake by college-age young adults is particularly important to understand.

Despite hundreds of studies in the literature, the value of calcium supplementation remains controversial. Two recent reviews took opposite positions. One review of existing evidence concluded that supplements are effective (Herbert V. Vitamins and Minerals plus Antioxidant Supplements. in *Total Nutrition,* ed. Herbert V, Subak-Sharpe G J. New York: St. Martin's Press; 1995:112.), the other that they are not. (Kanis J A, Passmore R. Calcium Supplementation of the diet-1: Not justified by the present evidence. BMJ. 1989; 298:137–40.) Even in the review favoring use of supplements, practical recommendations for a particular dosage are absent.

A further study was undertaken with women over age 40 to begin to apply the method of elevated urinary excretion to determine calcium requirements for mature women to exemplify the general application of the invention to ascertaining the effective dosage of edible materials that are water-soluble, urine-excretable and nontoxic.

Early work established the value of the present invention with respect to Vitamin C. Vitamin C, ascorbic acid, has long been known to prevent scurvy and more recently has been shown to have an effect on the healing of wounds, the health of gums, and the strength of bones through the stabilization of collagen. See Davies, M. B. et al., "Vitamin C: Its Chemistry and Biochemistry," Cambridge, Royal Society of Chemistry, 1991, pp. 7–25; Stare, F. J. and I. M. Stare, "Charles Glen King, 1896–1988," J. Nutr., 118:1272–7, 1988; and Roig, M. G. et al., 'IL-Ascorbic Acid: an Overview," Int. J. Food Sci. Nutr., 44:59–72, 1993. However, other possible health benefits, including prevention of cancer (see Roig, supra; Block G., "Vitamin C, Cancer and Aging," Age, 16:55–8, 1993; Marwick, C., "Cancer institute Takes a Look at Ascorbic Acid," JAMA, 264:1926, 1990; and Wittes, R. E., "Vitamin C and Cancer," New Engl. J. Med., 312:178–9, 1985), prevention of heart attacks and reduction of cholesterol (Burr, M. L. et al., "Incidence for Premature Rupture of Membranes in Pregnant Women with Low Leukocyte Levels of Vitamin C," Eur. J. Clin. Nutr., 39c:387–8, 1985; Kimura, H. Et al., "Dietary Ascorbic Acid Depresses Plasma and Low Density Lipoprotein Lipid Peroxidation in Genetically Scorbutic Rats," J. Nutr., 122:1904–9, 1992; and Uchida, K. Et al., "Effect of Vitamin C Depletion on Serum Cholesterol and Lipoprotein Levels in ODS (od/od) Rats Unable to Synthesize Ascorbic Acid," J. Nutr., 120:1140–7, 1990), and as a boost to the immune system to prevent colds (Blanchard, J. et al. "Comparison of Plasma, Mononuclear and Polymorphonuclear Leukocyte Vitamin C Levels in Young and Elderly Women during Depletion and Supplementation," Eur. J. Clin. Nutr., 43:97–106, 1989; Chavance, M. et al. "Vitamin Status, Immunity and Infections in an Elderly Population," Eur. J. Clin. Nutr., 43:827–35, 1989; Vallance, S., "Platelets, Leukocytes and Buffy Layer Vitamin C After Surgery," Hum. Nutr., 40c:35–41, 1986: and Vojdani, A. and M. Ghoneum, "In Vivo Effect of Ascorbic Acid Enhancement of Human Natural Killer Cell Activity," Nutr. Res., 13:753i, 1993), remain controversial.

The "free radical theory of aging" has been postulated to explain age-related cell damage in animals and plants. See Pryor, W. A., "The Formation of Free Radicals and the Consequences of their Reactions in vivo, "Photochem. Photobiol., 28:787–801, 1978; and Harman, D., "The Aging Process," Proc. Natl. Acad. Sci. USA, 78:7124–7128, 1981. Vitamin C appears to play a synergistic role with vitamin E in providing essential antioxidant protection (Tappel, A. L., "Vitamin E as the Biological Lipid Antioxidant," Vitam. Horm., 20:493–510, 1962; and Niki E. et al., "Inhibition of oxidation of Methyl-Linoleate in Solution by Vitamin E and Vitamin C," J. Biol. Chem., 259:4177–4182, 1984). Given the large number of "free radical" diseases, it is reasonable to assume that taking an optimal dose of vitamin C could be extremely beneficial, as suggested by Block, G., supra, and by Harman, D. in "Free Radical Theory of Aging: Current Status," Lipofuscin 1987: State of the Art, edited by I. Zs.-Nagy, New York, Elsevier, 1988, pp. 3–21. With around 20 million people in the U.S. taking daily supplements of Vitamin C, it is appropriate to determine what an optimal dosage would be.

Unfortunately, the optimal dose of vitamin C is not established. The recommended daily allowance sufficient to prevent scurvy varies from 30 mg in the United Kingdom to 60 mg in the U.S. and 90 mg in the former Soviet Union. In contrast, mega-doses of up to 16 g per day are suggested to provide additional health benefits.

In fact, the optimal dose of vitamin C depends on many factors. Vitamin C is water soluble and cannot be stored in the body to any great extent. However, when vitamin C is regularly ingested, a body pool develops, which may become large even though some vitamin C is being excreted in the urine. Thus, it can take months of ascorbic acid deprivation for the body pool to become depleted to the point where symptoms of scurvy appear. Large-dose intake benefits may be small because of finite absorption from the intestine, limited metabolism by the liver, or excretion by the kidney. For example, it has been reported that only about 60% of a 500 mg dose is normally absorbed into the body of an average person within the first 12 hours after ingestion, while 40% is excreted prior to metabolization (see Olson, J. A., and R. E. Hodges, "The Scientific Basis of the Suggested New RDA Values for Vitamins A and C," Nutr. Today, 20:14–15, 1985). In fact, it has been ascertained that a certain percentage of any dose is always excreted, and that such percentage increases with the dose (see Blanchard, J. et al., "Effects of Age and Intake on Vitamin C Disposition in Females," Eur. J. Clin. Nutr., 44:447–460, 1990).

Without a clear physiological endpoint to measure an optimal dosage or a complete understanding of the functional role of vitamin C, it is unclear how much vitamin C one should take. Because large doses are not entirely absorbed and may even irritate a patient's stomach, and because small doses may be insufficient to provide sufficient antioxidant protection, there exists a need to determine a dosage sufficiently large to ensure as large as possible a presence in the body while at the same time minimizing excesses and waste through excretion. This invention provides a method that fulfills this need by ensuring that some excess vitamin C is always present in the urine of a user.

SUMMARY OF THE INVENTION

This invention is embodied in a test kit for determining the optimal level of intake for an individual of a useful substance that is water soluble, urine excretable, and non-toxic at physiologically beneficial levels. The test kit may include, a container for holding a sample of urine from the individual being tested, a reagent for reacting with an amount of the substance for which the test is conducted in a sample of urine from the individual, and an indicator for indicating to the user of the kit the concentration of the substance in the sample of urine in response to a reaction between said reagent means and said amount of said substance.

In one embodiment, the test kit is used for determining the optimum dosage of vitamin C. In this embodiment, the reagent may comprise phosphoric acid, a buffer of trisodium citrate dehydrate, and vitamin C and the indicator may be 2,6-dichlorophenolindophenol dissolved in water.

In another embodiment, relating to the oral administration of water-soluble, urine-excretable, nontoxic edible composition to a person, the invention comprises a method for producing a continuously-saturated level of at least one such water-soluble, urine excretable, nontoxic edible composition in the body of the person. The method comprises the steps of administering a predetermined dose of such water-soluble, urine excretable, nontoxic edible composition to the person at a predetermined time; monitoring the concentration level of a water-soluble, urine excretable, nontoxic edible composition in the urine of the person to record any increase thereof during a 24 hour period following said predetermined time; increasing said predetermined dose by a predetermined amount and repeating the preceding until a threshold dose is found that produces a sustained increase in said concentration level of such water-soluble, urine excretable, nontoxic edible composition in the urine of the person for a duration of time at least as long as a predetermined period; and, thereafter, administering no less than said threshold dose of a water-soluble, urine excretable, nontoxic edible composition to the person at intervals not larger than said duration of time.

The invention is also embodied in a method of elevated urinary excretion for determining a useful dosage of calcium, which consists of collecting and analyzing every micturition for periods of time at different dose rates, and determining for one or more individuals the rate and dose (dosage) necessary to elevate the level of urinary excretion continuously over a period of time.

Another such method is the method of urinary excretion as used for determining a useful dosage of any water-soluble, excreted in the urine, non-toxic at useful levels substance, such as vitamin C, calcium, other vitamins such as the B-vitamins, other minerals such as iron, and other substances such as aspirin in the form of itself or distinct metabolites such as salicylic acid.

The invention may be embodied in pills, solutions, or other means of delivering the optimum dosage determined for the individual or for a class of individuals. For example, the invention may be embodied in a 200 mg calcium pill designed to be taken every 12 hours for people aged 18–23.

The invention may also be embodied in pills, solutions, or other means of delivering the approximate dosage for a combination of substances, such as a pill containing 200 mg of calcium and 500 mg of vitamin C, or 200 mg vitamin E and 500 mg vitamin C, designed to be taken twice a day; or multiple pills such as 100 mg calcium and 250 mg vitamin C pills designed to be taken twice in the morning and twice at night. Of course, pills similar those described may be used, differing, for example, only slightly in the quantity of material included. An example would be a pill containing 200 mg of calcium and 400 mg of vitamin C or 150 mg of calcium and 400 mg of vitamin C, which will achieve approximately the same effect of elevated urinary excretion in some individuals by the described method.

The invention may be embodied in a kit consisting of a device or solutions or test strips which can be used by an individual, health practitioners, or device for an individual to apply the method of urinary excretion to determine the dosage of calcium necessary for an individual to achieve elevated urinary excretion. Such a kit may comprise, for example, plastic strips with pads at one end to be dipped in urine containing an indicator for calcium, which produces a calorimetric response over the range of common physiological concentration of calcium in urine. Such strips would be used for every micturition over a period of time so that the individual can compare the results at different times and doses of calcium to determine the dose and rate necessary to achieve elevated urinary excretion, or to determine that a particular dosage is effective in producing elevated urinary excretion.

Likewise, the invention may be embodied in a kit consisting of a device or solutions or test strips which can be used by an individual, health practitioners, or device for an individual to apply the method of urinary excretion to determine the dosage of other substances necessary for an individual to achieve elevated urinary excretion. Examples of such kits would be kits specifically designed to determine a useful level of aspirin as a blood thinner to prevent heart disease, and for other water-soluble vitamins and minerals such as cystiene, zinc, and selenium, which may be antioxidants and for many other useful substances fitting the three criteria of water solubility, excretion in urine, and non-toxicity at physiologically beneficial levels.

BRIEF DESCRIPTION OF THE DRAWINGS

FIG. 1 is an illustration of the relationship between daily doses of vitamin C and total urinary excretion of vitamin C during the 24-hour period following intake.

FIG. 2A graphically depicts data showing, for Individual 1, the rate of excretion of vitamin C during beginning and end 24-hour periods of separate eight-day cycles of a single daily intake of two grams.

FIG. 2B graphically depicts data showing, for Individual 2, the rate of excretion of vitamin C during beginning and end 24-hour periods of separate eight-day cycles of a single daily intake of two grams.

FIG. 2C graphically depicts data showing, for Individual 3, the rate of excretion of vitamin C during beginning and end 24-hour periods of separate eight-day cycles of a single daily intake of two grams.

FIG. 3 illustrates the effect of two daily doses of vitamin C for maintaining a measurable excess in a taker's urine.

FIG. 4 shows the effect on excretion of vitamin C following a regimen of two daily doses of 500 mg each taken 12 hours apart.

FIG. 5 shows the effect of two daily doses of 500 mg of vitamin C taken for two periods of eight consecutive days each.

FIG. 6 depicts data derived from the study of calcium requirements of young men and women and depicts data showing the total 24-hour urinary calcium excretion after intake of a single calcium supplement.

FIG. 7 depicts data derived from the study of calcium requirements of young men and women and depicts data showing the rate of urinary calcium excretion after intake of a single calcium supplement.

FIG. 8 depicts data derived from the study of calcium requirements of young men and women and depicts data showing the effect of a dosage of 100 mg of calcium twice daily on urinary calcium excretion.

FIG. 9 depicts data derived from the study of calcium requirements of young men and women and depicts data showing the effect of a dosage of 200 mg of calcium twice daily on urinary calcium excretion.

FIG. 10 depicts data from tests on young men and women showing the effect of a dosage of 300 mg of calcium twice daily on urinary calcium excretion.

FIG. 11 depicts data from tests on young men and women showing the effect of a dosage of 400 mg of calcium twice daily on urinary calcium excretion.

DESCRIPTION OF THE PREFERRED EMBODIMENTS

Figure 12:
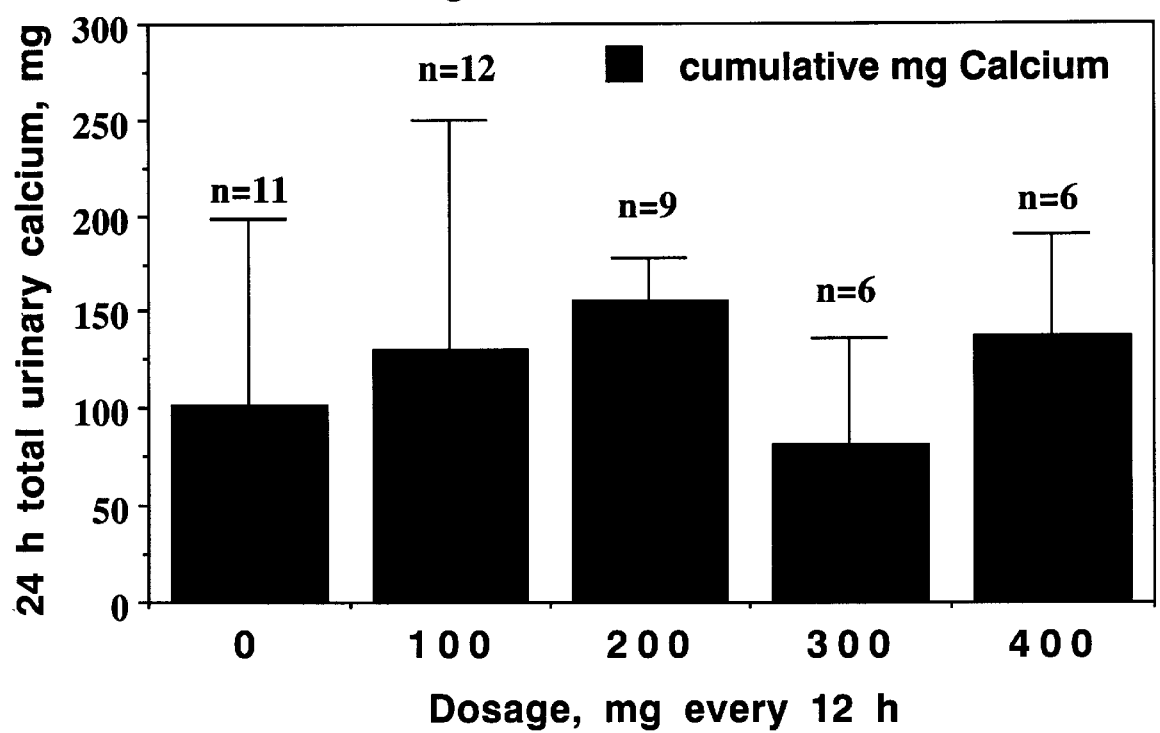
FIG. 12 depicts data from tests on young men and women summarizing the effect of different dosages of calcium twice daily on urinary calcium excretion.

The present invention amounts to a finding of the minimum rate of intake of ascorbic acid required to provide continuous optimal antioxidant protection to an average individual. The invention also discloses a general method for determining such optimal dosages and intake regimens for water-soluble vitamins and other nutritional supplements and medicines that require elevated concentrations in the blood stream for optimal effect.

Vitamin C Example

Because vitamin C has been implicated in a variety of diseases, it has been the subject of frequent clinical studies. These studies have compared subjects taking vitamin C on a "regular daily basis" with those not taking vitamin C. However, because vitamin C is a water-soluble vitamin, high doses are readily excreted in the urine, thereby quickly depleting the system to blood concentrations well below saturation.

With reference to vitamin C, saturation is defined herein as the level in an individual's blood stream above which vitamin C is excreted into the urine. Thus, the work that resulted in this disclosure was undertaken to determine what daily dose of vitamin C is necessary on average to produce a measurable level of vitamin C excretion in urine; whether a single dose, even a very high one, is sufficient to maintain measurable excretion at all times during an entire 24-hour period; and whether taking a regular daily dose of vitamin C leads to any noticeable change in vitamin C excretion over time.

The following procedures were followed in the experiments that generated the data shown in the figures.

I. Stability of Vitamin C in Water and Urine

To determine whether vitamin C is stable in urine prior to assay, stock solutions of vitamin C in water and in urine were prepared 48, 24, 12, and 0 hours before running standard curves using the DCIP procedure referenced below. Each stock solution contained 125 g of vitamin C/ml of 5% phosphoric acid in water or urine. The samples were stored in the dark at room temperature. The vitamin C degraded when stored in aqueous solutions of 5% phosphoric acid, but was stable in solutions containing urine in 5% phosphoric acid.

II. Effect of Dose of Vitamin C on Total Urinary Excretion

In order to determine how daily dosages related to total excretion and whether high daily doses would alter the rate of excretion after a week, groups of test subjects took either 0, 0.25, 1, or 2 gram doses of vitamin C at 8 a.m. daily for 8 consecutive days. All urine was collected and pooled on day 1 and on day 8. The concentration was assayed and the total amount of vitamin C excreted during the 24-hour period was determined, as shown in FIG. 1. The figure shows that the rate of urinary excretion of vitamin C increased with increasing daily doses of vitamin C, and that the amount excreted was similar even after taking it for 8 consecutive days.

III. Rate of Excretion of a Single Dose of vitamin C

In order to determine how rapidly vitamin C is excreted, several individuals took 2 grams of vitamin C daily (single dose) for 8 consecutive days, and collected samples and measured the volume of every micturition during the first and last day. The experiment was repeated with the same individuals after a seven day rest. Each sample was analyzed to determine the time period, concentration range, and total urinary excretion of vitamin C. The results are shown in FIG. 2 for three representative individuals. Vitamin C concentration in the urine increased after 4 hours from time of intake and remained elevated for a total of 12 hours, consistent with the hypothesis that vitamin C levels in the body are not elevated for an entire 24 hour period by a single daily dose. However, only a small percentage of the ingested vitamin C was detected in the urine. No noticeable difference in the excretion pattern during the first and last days was observed.

IV. Effect of Twice-Daily Doses of Vitamin C on Urinary Output

Because it was found that a single dose of vitamin C elevates urine levels for only 12 hours and that a 500 mg dose is sufficient to provide detectable levels in the urine, one individual took doses from 250 to 2000 mg of vitamin C every 12 hours to determine whether vitamin C levels would remain continuously elevated. FIG. 3 shows that a dose of 250 mg did not cause detectable excretion in amounts exceeding normal quantities, but doses of 500 mg or higher provided continuously detectable elevated levels of excretion, with higher levels corresponding to higher doses. Twice-daily doses of 500 mg were sufficient to elevate vitamin C in the urine continuously as shown for 5 individuals in FIG. 4. When 500 mg are taken twice daily for a week, vitamin C remains continuously elevated on the first and last day, as shown for two such periods in FIG. 5.

Assay Procedures

Vitamin C was assayed by the 2,6-dichlorophenolindophenol (DCIP) assay (see Omaye, T. S. et al. "Selected Methods for the Determination of Ascorbic Acid in Animal Cells," in Methods Enzymol.: Vitamins and Coenzymes, Vol. 62, edited by McCormick, D. B. and L. D. Wright, New York, Academic Press, 1979, pp. 3–11). Samples diluted to 0–40 micrograms ascorbic acid with 5% phosphoric acid were assayed in a citrate/acetate buffer by reaction with DCIP, and the color at 520 nm compared with standards. Samples were assayed in duplicate and each experiment was repeated. The ascorbic acid standard was from Gibco Laboratories, and the 500 mg of vitamin C pills used were the brand marketed by Leiner Health Products, Inc., of Torrance, Calif., under the trademark "YOUR LIFE." The pills were assayed for vitamin C content by extraction by grinding in 5% phosphoric acid and were shown to contain the appropriate quantity of ascorbic acid.

We found that a one-time dose of 500 mg is necessary for detectable excretion in most individuals. As shown in FIG. 1, doses of less than 0.5 g per day did not cause significant vitamin C levels in urine, even when taken for 8 consecutive days. Vitamin C was administered daily to five individuals at 8 a.m. for eight consecutive days. All urine for each individual was collected during the first and last 24-hour periods and the total amount of vitamin C excreted in the urine was determined by DCIP assay. Doses of 500 mg to 2 g resulted in increased levels of urinary vitamin C, so that it was readily detectable, but only for approximately 12 hours even at the highest rate of intake. The figure shows that traces of ascorbic acid may be found in human urine at all times, even when no vitamin C has been administered in pills. A consistently elevated level (greater than the standard deviation of the measurement SD) is found to begin at intake rates between approximately 250 and 500 mg per day, thus showing that lower rates do not produce a saturated condition in the blood stream at all times.

FIG. 2 illustrates the effect of two grams of daily single-dose vitamin C taken orally for eight days, followed by six days with no intake, and then by eight more days of two grams taken daily in a single dose. Each micturition during the first and last 24 hours of each eight-day period was collected and assayed to determine the total mass of vitamin C excreted. FIGS. 2a–2c represent excretion from three different individuals. Despite variations among the different subjects, FIG. 2 shows that taking two grams daily for eight days did not lead to any noticeable difference in the pattern of excretion from day to day for any of the subjects. This demonstrates that even a high single daily dose is inadequate to maintain an elevated rate of urinary excretion of vitamin C on a continuous basis.

In order to achieve such sustained presence of vitamin C in urine, it is instead necessary to take it at least twice daily, as shown in FIG. 3. Different dosages (from 0.25 to 2.0 grams) of vitamin C were administered to a representative subject every 12 hours, at times 0 and 12 hour in the figure, on four separate days of a four-week period. The mass of vitamin C present in the urine was measured at every micturition. The individual was tested one day of the week for four consecutive weeks with progressively increasing dosages followed by six-day periods of rest. As illustrated by the figure, taking at least 500 mg twice daily led to continuously elevated levels of vitamin C in the urine tested.

FIG. 4 shows the results on five individuals who took 500 mg of vitamin C at time 0 and 12 hour during a 24-hour period. Each micturition during the entire 24 hours was collected and the total mass of vitamin C excreted by each subject was measured by the DCIP assay. In yet another experiment, two daily doses of 0.5 grams of vitamin C were taken daily for 8 days, then no pills were taken for a week, and then 0.5 grams daily were taken again for another 8 days. Each micturition during the first and last 24 hours of each 8 day period was collected and assayed to determine the total mass of vitamin C excreted. As seen in FIG. 5, the level of excretion was similar during the first and eighth day of testing (demonstrating that no appreciable cumulative effect occurred).

These results have important implications for dietary purposes and for the design of clinical studies involving vitamin C. First, small doses of vitamin C are unlikely to provide elevated vitamin C levels in the body, particularly in the blood. Therefore, optimal antioxidant protection cannot be achieved below a minimum dosage threshold, found to be at about 500 mg per dose. At this point it is still unclear whether doses below 500 mg/dose are absorbed or metabolized, but the evidence clearly supports the conclusion that at least 500 mg/dose is necessary to saturate the blood sufficiently for vitamin C to appear in the urine.

Second, although 500 mg/dose is sufficient to produce vitamin C excretion, a single dose of even 2 g/day is insufficient to maintain excretion over a 24 hour period. Therefore, if a continuous protective effect is desired or if a study is intended to determine particular protective effects of vitamin C, it is necessary that the vitamin be administered at least every 12 hours.

The precise role of vitamin C in maintaining good health remains to be understood, but a large body of evidence is consistent with the hypothesis that individuals taking doses of vitamin C substantially greater than the USDA Recommended Daily Allowance may have a substantial health benefit. Until the precise role of vitamin C becomes clear, it may be prudent to take a dose which is large enough to produce continuously detectable excretion, but not so large as to cause digestive-system discomfort or other problems. The results of the present work support the conclusion that in order to continuously maintain measurable levels of vitamin C in urine, at least 500 mg of vitamin C should be taken at least twice daily (every 12 hours).

This work also demonstrated a useful tool to determine optimal dosages and regimens for water soluble-substances that are desirable in elevated concentrations in the blood stream. By measuring the concentration of such a substance in urine after ingestion of a predetermined dosage and according to a predetermined regimen, one can find an intake threshold below which the substance is not maintained above saturation, thereby setting a minimum dosage and rate of administration for continuous saturation in the blood pool of an individual. The dosage and regimen for a variety of physiologically and medically useful substances clearly vary for different individuals, depending on many personal characteristics such as age, weight, health, and gender. For nutritional supplements such as vitamins and minerals and for medicines such as aspirin, which are water-soluble, are excreted in urine, and are nontoxic at physiologically beneficial levels, monitoring detectable urinary excretion is a means to establish a potentially medically and/or nutritionally useful dosage and regimen. The method involves taking different dosages of substance at different frequencies and testing the urine to determine whether the substance is present in every micturition.

This method could also involve a variety of products specific to the substance being tested. For example, test strips containing individual pads of reactive materials could be used to check a urine specimen to determine whether a detectable quantity of a particular substance, such as vitamin C, salicylic acid, cystiene, zinc, or selenium, is present. Similarly, dropper kits would permit a person to add drops of certain substances to a urine specimen to determine whether a given substance is present in the urine at a detectable concentration.

For example, a kit for determining whether an individual is taking a sufficient amount of vitamin C for a significant excess to be detected in the urine could consist of the following components:

1. A dropper bottle, labeled Acid, containing a given quantity, such as 10 ml, of 10% phosphoric acid, fitted with a dropper graduated at 0.6 ml.
2. A dropper bottle, labeled Buffer, containing a commensurate quantity, such as 10 ml, of citrate/acetate buffer, pH 4.15 (made with 2.2 g of trisodium citrate dehydrate), fitted with a dropper graduated at 0.6 ml.
3. Two screw capped test tubes labeled 1 and 2 with graduations at 0.6 ml, 1.2 ml, 1.8 ml, and 2.4 ml.
4. A dropper bottle at least 10 ml in capacity and containing 1 mg of dry 2,6-dichlorophenolindophenol, labeled DCIP and fitted with a dropper graduated at 0.6 ml.
5. A bottle containing a commensurate quantity, such as 10 ml, of distilled water, labeled Water.
6. A packet of vitamin C crystals (10 mg) labeled Vitamin C crystals.
7. A plastic cup with a wide top, about 5 ml in volume, with a pour lip similar to a beaker, labeled Collection Cup.

Such a kit is designed to permit a user to determine whether he or she is getting enough vitamin C in the diet to be able to maintain a continuous excretion of vitamin C in the urine. To be accurate, one should use this test throughout a single 24-hour period, testing a sample at each time of urination, to see whether a sufficient amount of vitamin C is kept in the system to be detected all day long. Because excess vitamin C in the diet may be excreted by the kidneys within 12 hours of reaching the bloodstream, it is important to monitor its presence in the urine during an entire 24-hour period while consuming a typical diet. This kit is designed to allow one to do so safely and conveniently, using a single kit for an entire 24 hour period.

The kit is used as follows. At the start of the 24-hour period during which one intends to test vitamin C excretion, the bottle of water is opened and emptied into the dropper bottle labeled DCIP, and the combined contents are shaken for about 1 minute until all solids are completely dissolved, producing a blue DCIP solution.

A small sample of urine is collected in the Collection Cup each time the individual urinates during the following 24 hours. Test tube 1 is filled up to the level of the first mark (0.6 ml) with the urine so collected. Then all further additions are made to test tube 1.

One dropper full (up to the 0.6-ml mark) of Acid is added to test tube 1, which already contains the urine sample. Next, one dropper full (0.6-ml) of Buffer is added to test tube 1 (up to the 1.2-ml mark). The cap is placed on test tube 1 and the contents are mixed by inverting the test tube at least three times.

The contents of the test tube are then tested to check if there is any vitamin C in the urine. Test tube 1 is opened and one dropper-full (0.6 ml) of DCIP solution is added (up to the 1.8-ml mark). If the bluish color of the DCIP solution immediately disappears, vitamin C is present in the urine. If instead a pink color appears and persists for more than 15 seconds, the cap is replaced and the tube inverted several times for mixing. If the pink color now disappears, it is an indication that some vitamin C is excreted in the urine. If the pink color still persists, or if the color cannot be seen clearly because of the color of the urine itself, the procedure is continued as follows.

Half the contents of test tube 1 are poured into test tube 2, so the two solutions are divided approximately evenly between the two tubes. The packet of Vitamin C crystals is opened and a few crystals (one to three) are sprinkled into test tube 1. The tube is capped and its contents mixed by inverting it at least three times.

The colors of tube 1 and tube 2 are now compared. If the two tubes are identical in color, it is an indication that a sufficient amount of vitamin C is being consumed and that the urine sample being tested contains excess vitamin C. If tube 2 is darker or more strongly pink than tube 1, then it is an indication that no excess is present and that possibly one would benefit from consuming additional vitamin C through a better diet or vitamin supplements.

This test is repeated at each micturition during the chosen 24 hour period. Because vitamin C is excreted rapidly from the body, vitamin C is unlikely to be present in urine more than 16 hours after a good source of vitamin C is last consumed. Therefore, one should check for an entire 24-hour period to determine if enough vitamin C is being consumed on a regular basis to keep a continuously-elevated level in the urine.

The kit and procedure just described represent a simple method for implementing the concept of this invention. However, many similar strategies and devices could be used to achieve the same end. For instance, the reagents could be attached in powder form to a stiff, insoluble, plastic stick, such that all of the reagents except the dye would dissolve off of the stick when stirred in a small cup of urine, and then the test stick removed, and the color of the stick would indicate the presence or absence of vitamin c by the change in the dye-containing region of the stick. Note also that certain substances present in the urine of some individuals may interfere with the results of the test. For instance, consumption of beets will turn urine temporarily red, which will make it difficult to observe any results clearly.

A person could use this method, implemented through a product as described above, as a simple indication of whether a sufficient dosage and regimen of a substance were being taken to ensure the presence of a minimum useful excess of the desired substance in the body at all times. The method could similarly be used by researchers to gather data for a variety of substances by age, weight, and other criteria, to establish a dosage which would ensure the presence of a minimum useful excess of a substance in the body. As is known for vitamin C, 60 mg daily will prevent scurvy, but much higher doses may be required to improve health, such as by preventing a variety of adult disorders not readily connected with a lack of vitamin C. By application of the method of the invention, 500 mg of vitamin C twice daily has been determined to provide a sufficient dose to have excess vitamin C excreted.

Calcium Example

The method of this invention was applied to the determination of optimum calcium levels for two groups, young men and women and mature women. In the first example, the minimum dosage of calcium supplements necessary to increase urinary excretion above control levels for young men and women was determined. Consuming their normal diets, nineteen people ages 19–24 were given doses of calcium from 0 to 1,500 mg for 1 to 7 days. Every urine sample was collected and analyzed by atomic absorption spectroscopy. Students taking a single dose of 250 mg excreted more than controls over a 12 hour period, and higher doses did not cause higher excretion. When two doses per day were taken, only doses over 100 mg gave elevated excretion over 24 hour periods. Thus, a dose of approximately 200 mg every 12 hours may be suitable for those who take supplements.

This study was undertaken to determine a practical recommendation for calcium supplementation in typical college students ages 19–24. Given that most people do not get sufficient calcium in the diet to achieve the Daily Value of 1,000 mg per day, what dosage of calcium supplements is effectively absorbed? Especially for individuals with a family history of osteoporosis, what guidance can a health professional provide?

Elevated urinary excretion of calcium has been shown to reflect its increased absorption. Measurement of urinary calcium levels thus provides a convenient way to determine a useful level of supplementation. The Applicant previously determined a useful dosage of vitamin C using the method of urinary excretion, as disclosed in U.S. patent application Ser. No. 08/317,311, filed Oct. 3, 1994, a result confirmed by a major study at the National Institutes of Health. In this study, the Applicant has used the same method to determine a practical dosage of calcium.

Methods

Nineteen volunteers (16 females, 3 males, ages 19–24, weight range 116–234 lbs., average 157 lbs.) were screened for risk factors after discussing and signing an informed consent statement approved by the Institutional Research Board. During each experiment, each person measured the volume and saved a sample of every micturition and kept a record of all additional sources of calcium in the diet in addition to supplements.

Urine samples were analyzed for calcium by atomic absorption spectroscopy (AA), in accordance with the manufacturer's protocol (Perkin Elmer 360 Atomic Absorption Spectrophotometer). Standards (0–50 mg/liter) and samples were diluted in 5% lanthanum/5% potassium chloride. Each sample was analyzed five times and the average absorption compared with the standard curve.

Results

Valu-Rite Natural Oyster Shell Calcium 500 mg (McKesson Corp., San Francisco, Calif.) for the single dose study were in the form of calcium carbonate, and analysis indicated an actual content of 550 mg. Relief Plus Calcium Antacid (K Mart Corp., Troy, Mich.) for the multiple dose study was labeled 200 mg calcium in the form of calcium carbonate, and analysis indicated an actual calcium content of 220 mg.

In the first study, volunteers were divided into groups of three. After one day without taking any calcium supplements, each student took a single dose of 0, 250, 500, 1,000, or 1,500 mg, and collected samples for the following 24 hours. Of those taking 1,000 or 1,500 mg, five of six complained of unpleasant side-effects including diarrhea and nausea.

As shown in FIG. 6, which depicts the average 24 hour excretion levels of calcium, while there is large individual variation in absorption of calcium, there appears to be no benefit to a single dose of 500 mg or higher, which is the level of many commercially available calcium supplements, and the potential side effects and risk factors for many people make such doses inappropriate.

Data from every micturition of each individual were combined to provide an average rate of excretion for every 6 hour period from ingestion of the supplement. The results, shown in FIG. 7, indicate that urinary excretion rises over the initial 12 hours after consumption of the pill. To obtain maximum absorption, it is therefore useful to consume a pill every 12 hours.

Based on the single dose study showing supplementation every 12 hours at a dose below 500 mg may be most effective, volunteers were divided into groups of 4 and given 100, 200, 300, or 400 mg of calcium to take twice daily. On day 0, no supplements were taken. On day 1, no supplements were taken and samples were collected to provide control levels of excretion. On days 2–8, supplements were taken twice daily and samples collected on days 2, 7, and 8.

Because the rate, concentration and quantity of calcium excreted in the urine depends upon a host of factors and is highly variable, the data was analyzed by calculating the total cumulative calcium excretion during each 24 hour period, and averaging data for the three days when supplements were taken. When analyzed this way, elevated excretion is apparent, as seen in FIGS. 8–11, which present examples of individuals taking 100–400 mg of calcium as supplements twice daily. However, results varied considerably from one individual to the next, with only 9 of 11 subjects completing the protocol showing increased excretion, and only 7 of 11 showing continuously elevated levels of excretion after the initial 4 hours of collection. Of the five not completing the protocol, four were at a level of 300 or 400 mg and reported nausea or diarrhea.

Comparison of the total average 24 hour excretion for all data is shown in FIG. 10. As was seen for the single dose data in FIG. 6, dosages above 200 mg twice daily appear to offer no advantage, and are more likely to cause unwanted side effects such as diarrhea and nausea.

Reviews of the scientific and medical literature on calcium and osteoporosis indicate that to reduce one's risk for osteoporosis, regular exercise, quitting smoking, protein intake restricted to the Daily Value of 60 g, and minimal sodium intake are beneficial. However, because available consumption per capita is 920 mg compared to the Daily Value recommendation of 1,000–1,500 mg, and young women in the United States obtain an average of only 500 mg of dietary calcium compared to the Daily Value of 1,000 mg, it would be useful to know from what level and form of calcium supplement a prudent individual might benefit.

Because there is no answer to this question in recent major reviews on calcium supplements, the present study was undertaken to determine what level of supplementation would provide increased absorption of calcium, as indicated by elevated levels of urinary excretion. I hypothesized that a desirable level of supplementation would have two characteristics: 1) an elevated level of urinary excretion, indicating increased absorbance from the intestine, and 2) a low level of supplementation, avoiding as much as possible the harmful side effects and risks associated with supplements.

Although the sample size used in this study was limited, the method and results obtained indicate that a useful answer can be obtained by the strategy we have employed. For the data gathered thus far, a dosage of 200 mg twice daily appears to be the prudent recommendation. FIG. 7 shows that the elevated excretion lasts for a period of 12 hours, supporting our recommendation of taking supplements twice a day. FIG. 10 shows that taking a dose of approximately 200 mg each time will increase absorption of calcium without taking more hazardous higher doses.

People who have risk factors associated with taking calcium, those who pay attention to their dietary intake and achieve a Daily Value of 1,000 mg, or those who have had specific analyses for calcium in their diet are fortunate to know how much calcium to take. For those young people who are uncertain, until further data are obtained, a dosage of 200 mg of supplemental calcium every 12 hours is appropriate.

As pointed out above, a further study was undertaken with women over age 40 to begin to apply the method of elevated urinary excretion to determine calcium requirements for mature women to exemplify the general application of the invention to ascertaining the effective dosage of edible materials that are water-soluble, urine-excretable and nontoxic, in addition to the analysis for students ages 18–23 presented above. These data are depicted graphically in FIGS. 13–16. The data show how this method can be applied to other groups such as premenopausal mature women and post-menopausal women who may or may not be taking drugs such as Fosimax and/or estrogen which may lead to the determination of different requirements for supplemental calcium to achieve saturation as indicated by maximum elevated urinary excretion.

Figure 13:
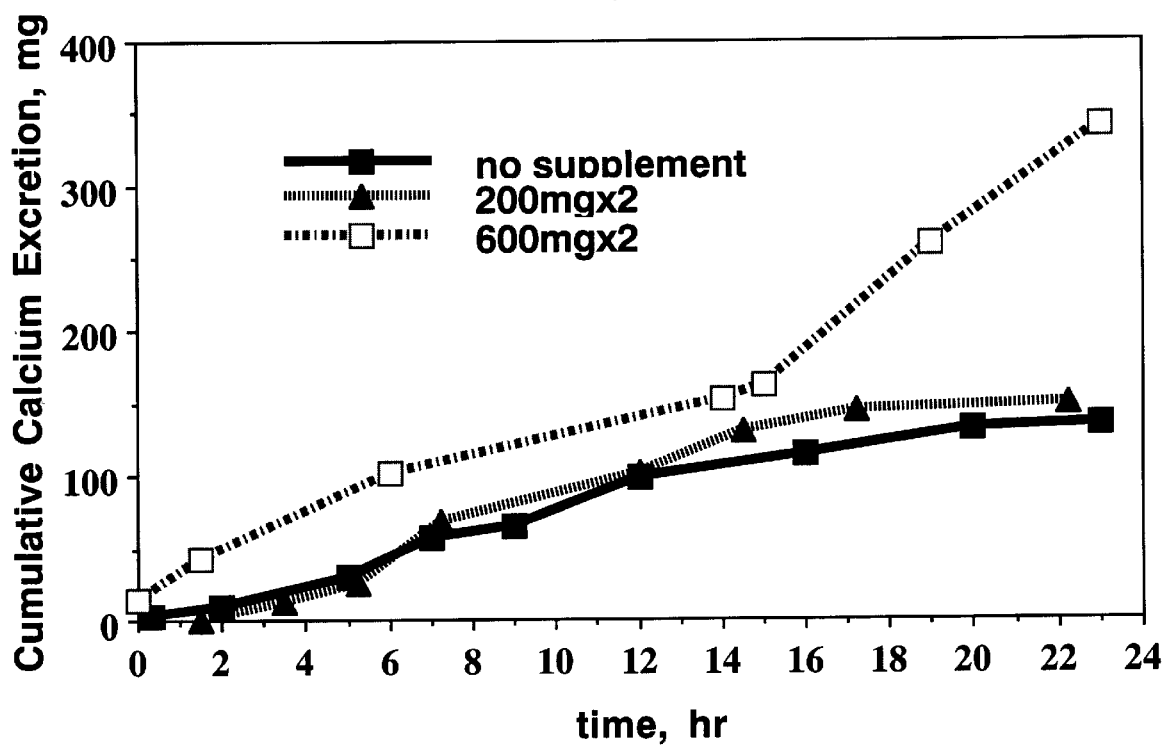
FIG. 13 depicts data derived from a test conducted on a pre-menopausal woman indicating that, for this individual, approximately 400 mg twice a day is necessary to obtain elevated urinary excretion.

Referring to the data graphically depicted in FIG. 13 with respect to a pre-menopausal woman, It can be seen that for this individual, a supplement of approximately 400 mg twice a day is necessary to obtain elevated urinary excretion.

Figure 14:
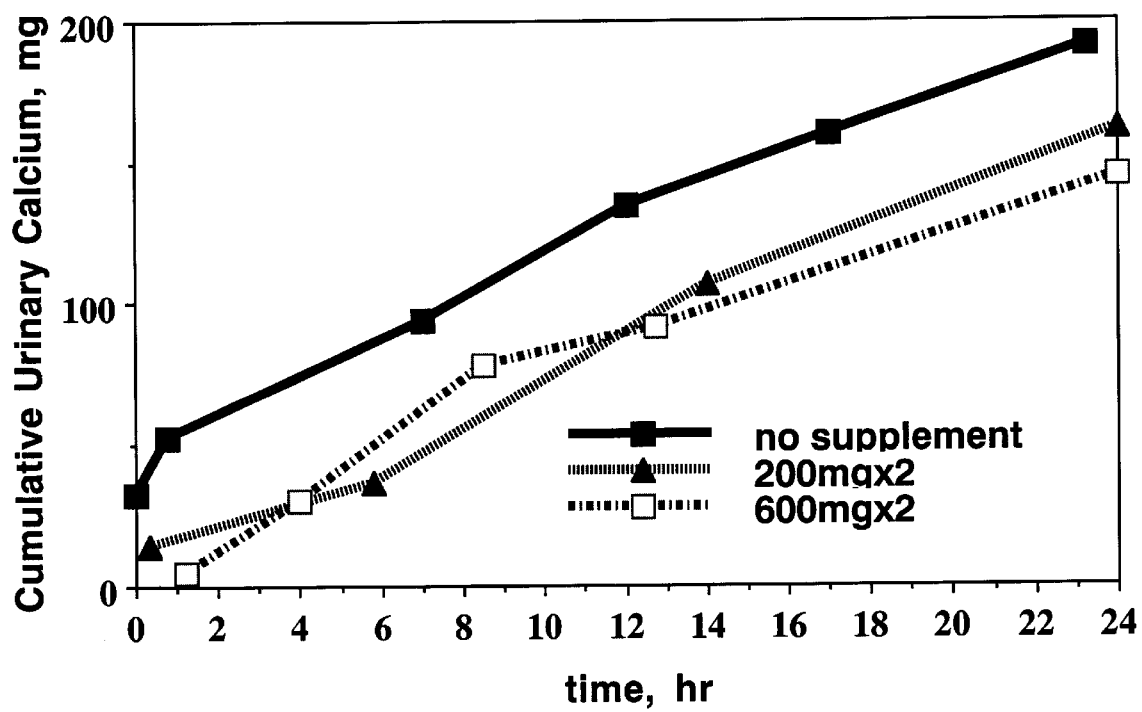
FIG. 14 depicts data derived from a test conducted on a post-menopausal woman with naturally elevated blood calcium indicating that this individual does not benefit and may actually be harmed by calcium supplements.

The data graphically depicted in FIG. 14 relate to a post-menopausal woman with naturally elevated blood calcium. It can be seen that this individual does not benefit and may actually be harmed by calcium supplements. The supplements reduce urinary excretion, which is likely caused by elevated intestinal calcium levels reducing the absorption of calcium.

Figure 15:
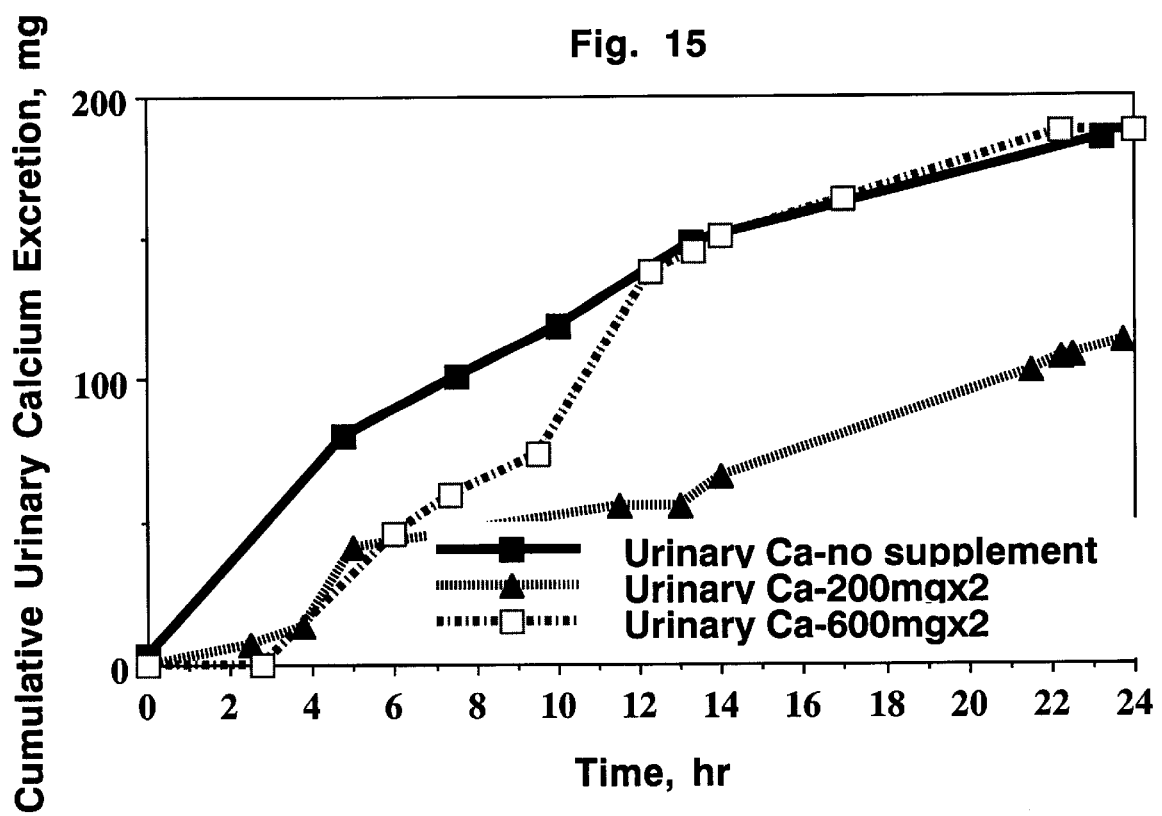
FIG. 15 depicts data derived from a test conducted on a postmenopausal woman taking Fosimax and indicate that for this individual a dose of 600 mg twice a day is too high and is inhibiting absorption.

The data graphically depicted in FIG. 15 relate to tests run on a postmenopausal woman taking Fosimax. This woman had previously been taking 600 mg three times per day. Results show that a dose of 600 mg twice a day Is too high and is inhibiting absorption. A lower dose would be safer and more useful.

Figure 16:
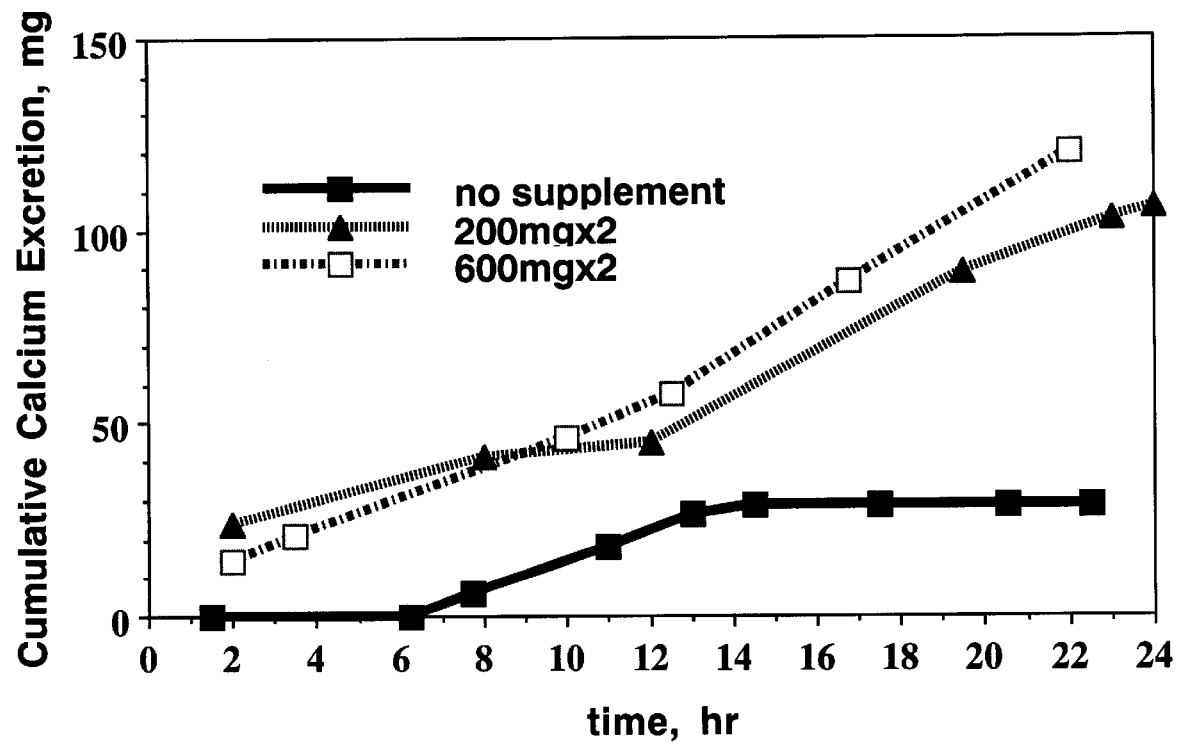
FIG. 16 depicts data derived from a test conducted on a postmenopausal woman not on medication indicating that 200 mg twice a day is sufficient to produce elevated urinary calcium, and that higher levels provide little extra benefit for the increased risks associated with higher calcium dosage.

The graphed data of FIG. 16 relate to tests on a postmenopausal woman not on medication. Results show that 200 mg twice a day is sufficient to produce elevated urinary calcium, and that higher levels provide little extra benefit for the increased risks associated with higher calcium dosage.

The above data demonstrate how the method of elevated urinary excretion can be applied to groups of people in addition to young people ages 18–23 as was demonstrated above.

General Applicability & Specific Embodiments

Having demonstrated the validity of the method and the utility of test kits by the above examples, it will be clearly apparent to those skilled in the art that the inventions are of general applicability as to any useful substance that is water soluble, urine excretable, and nontoxic at physiologically beneficial levels and, in general, ascertaining a dosage of any water-soluble, urine-excretable, nontoxic edible composition.

The invention may be embodied in any of several methods, all of which use the principle of the invention but may use different reagents, etc. One such method, of course, is the method of elevated urinary excretion for determining a useful dosage of calcium, which consists of collecting and analyzing every micturition for periods of time at different dose rates, and determining for one or more individuals the rate and dose (dosage) necessary to elevate the level of urinary excretion continuously over a period of time. An example of this is the study performed with students ages 18–23, in which students were given no calcium supplements, then a single dose of different quantities, which led to the determination that a dose of less then 500 mg was effective, and that it was effective for no more than 12 hours, etc. This differs from previous studies of urinary excretion of calcium in that every micturition was analyzed over a given time period and a practical dosage was determined by finding the dose necessary to produce elevated urinary excretion. Despite thousands of papers in the literature on calcium and calcium supplements, as demonstrated by literature citations to the article submitted as evidence, no one has applied this method or found any other way to suggest a useful level of calcium supplementation. The dosage of calcium determined by this method, in particular approximately 200 mg of calcium approximately twice a day for people ages 18–23, or other dosages to be determined for other groups such as pre-menopausal women, is seen in the examples presented.

Another such method is the method of urinary excretion as used for determining a useful dosage of any water-soluble, excreted in the urine, non-toxic at useful levels substance, such as vitamin C, calcium, other vitamins such as the B-vitamins, other minerals such as iron, and other substances such as aspirin in the form of itself or distinct metabolites such as salicylic acid.

The invention may be expressed in concept as pills, solutions, or other means of delivering the approximate dosage for calcium, for instance, a 200 mg calcium pill designed to be taken every 12 hours for people aged 18–23. No pill or solution is presently available which is designed to provide 200 mg calcium every 12 hours to meet the nutritional requirement for calcium, especially for young people.

Similarly, the invention may be embodied in pills, solutions, or other means of delivering the approximate dosage for calcium in combination with other substances, such as vitamin C, determined previously to have a useful dosage of 500 mg twice a day, such pill containing 200 mg of calcium and 500 mg of vitamin C designed to be taken twice a day; or multiple pills such as 100 mg calcium and 250 mg vitamin C designed to be taken twice in the morning and twice at night, thus delivering the claimed dosage of 200 mg of calcium and 500 mg of vitamin C twice a day; or pills similar to the above differing only slightly in the quantity of material included, such as a pill containing 200 mg of calcium and 400 mg of vitamin C or 150 mg of calcium and 400 mg of vitamin C which will achieve approximately the same effect of elevated urinary excretion in some individuals by the described method.

Of course, the invention may be embodied in a kit consisting of a device or solutions or test strips which can be used by an individual, health practitioner, or device for an individual to apply the method of urinary excretion to determine the dosage of calcium necessary for an individual to achieve elevated urinary excretion, such kit consisting of, for example, plastic strips with pads at one end to be dipped in urine containing an indicator for calcium, which produces a calorimetric response over the range of common physiological concentration of calcium in urine; such strips designed to be used for every micturition over a period of time so that the individual can compare the results at different times and doses of calcium to determine the dose and rate necessary to achieve elevated urinary excretion, or to determine that a particular dosage is effective in producing elevated urinary excretion.

Likewise, the invention may be embodied in a kit consisting of a device or solutions or test strips which can be used by an individual, health practitioner, or device for an individual to apply the method of urinary excretion to determine the dosage of calcium and other substances necessary for an individual to achieve elevated urinary excretion, such kit consisting of, for example, plastic strips with multiple pads at one end to be dipped in urine with one pad containing an indicator for calcium, which produces a calorimetric response over the range of common physiological concentration of calcium in urine; such strips designed to be used for every micturition over a period of time so that the individual can compare the results at different times and doses of calcium to determine the dose and rate necessary to achieve elevated urinary excretion, and another pad with an indicator for vitamin C; such kit to be used to determine useful dosages of more than one substance simultaneously, or to determine that a particular dosage of more than one substance is effective in producing the desired urinary concentration or elevation.

The above information describes the method and dosages of calcium supplements which are unique, useful, and not obvious. In addition, I describe here an example of a kit for applying this method which can be used by an individual, health practitioner, or device to determine the dosage of calcium necessary to produce an elevated level of urinary calcium. The kit consists of more than one test strip of plastic, onto one end of which is placed a pad saturated with an indicator which gives a color change proportional to the normal range of urinary calcium levels. The kit includes instructions for applying the method of elevated urinary excretion and a set of test strips, so that the person or device using the kit can determine the level of calcium in the urine over multiple micturitions, before and after taking various dosages of calcium, to determine whether the dosage results in elevated excretion of calcium.

The method may similarly be applied to determine a useful level of aspirin as a blood thinner to prevent heart disease, and for other water-soluble vitamins and minerals such as cystiene, zinc, and selenium, which may be antioxidants, for calcium, and for many other useful substances fitting the three criteria of water solubility, excretion in urine, and non-toxicity at physiologically beneficial levels.

Various changes in the details, steps and substances that have been described may be made by those skilled in the art within the principles and scope of the invention herein. Thus, while the present invention has been described herein in what is believed to be the most practical and preferred embodiment, it is recognized that departures can be made therefrom within the scope of the invention, which is not to be limited to the details disclosed herein but is to be accorded the full scope of the claims so as to embrace any and all equivalent apparatus and methods.

Industrial Application

This invention is useful in pharmacology, in the medical and veterinary product industries, and in the practice of medicine.

I claim:

1. In the oral administration of water-soluble, urine-excretable, nontoxic edible composition to a person, a method for producing a continuously-saturated level of at least one such water-soluble, urine excretable, nontoxic edible composition in the body of said person, comprising the following steps:

(a) administering a predetermined dose of said water-soluble, urine excretable, nontoxic edible composition to the person at a predetermined time;

(b) monitoring the concentration level of said water-soluble, urine excretable, nontoxic edible composition in the urine of said person to record any increase thereof during a 24 hour period following said predetermined time;

(c) increasing said predetermined dose by a predetermined amount and repeating steps (a) and (b) until a threshold dose is found that produces a sustained increase in said concentration level of said water-soluble, urine excretable, nontoxic edible composition in the urine of the person for a duration of time at least as long as a predetermined period; and (d) administering no less than said threshold dose of said water-soluble, urine excretable, nontoxic edible composition to said person at intervals not larger than said duration of time.

2. The method of claim 1, wherein said composition is an anti-oxidant.

3. A method of administration of vitamin C to a person ensuring that a continuously-saturated level thereof is produced in the body of the person, comprising the step of taking more than 250 mg of vitamin C approximately every 12 hours to produce a continuously-saturated level of vitamin C in the body of the person over a 24 hour period.

4. The method of claim 3, wherein about 500 mg of vitamin C is taken approximately every 12 hours.

5. In the oral administration of calcium to a person, a method for producing a continuously-saturated level of calcium in the body of said person, comprising the following steps:

(a) administering a predetermined dose of calcium to said person at a predetermined time;

(b) monitoring the concentration level of calcium in the urine of said person to record any increase thereof during a 24 hour period following said predetermined time;

(c) increasing said predetermined dose by a predetermined amount and repeating steps (a) and (b) until a threshold dose is found that produces a sustained increase in said concentration level of calcium in the urine of said person for a duration of time at least as long as a predetermined period; and (d) administering no less than said threshold dose of calcium to said person at intervals not larger than said duration of time.

* * * * *